United States Patent [19]

Lin et al.

[11] Patent Number: 5,352,251
[45] Date of Patent: Oct. 4, 1994

[54] FUEL COMPOSITIONS

[75] Inventors: Jiang-Jen Lin; James R. Macias; Earl J. Haury; Sarah L. Weaver; Charles L. Edwards; Pen-Chung Wang; Garo G. Vaporciyan, all of Houston, Tex.

[73] Assignee: Shell Oil Company, Houston, Tex.

[21] Appl. No.: 40,245

[22] Filed: Mar. 30, 1993

[51] Int. Cl.$^5$ .................. C10L 1/22; C07D 207/26
[52] U.S. Cl. ......................... 44/340; 44/329; 44/338; 44/353; 44/347; 44/415; 44/418; 44/432; 44/412; 540/362; 540/531; 540/451; 548/543; 546/243; 528/323
[58] Field of Search ............ 540/362, 531, 451; 548/543; 546/243; 44/329, 338, 353, 340, 339, 333, 347, 415, 418, 432, 412; 528/323

[56] References Cited

U.S. PATENT DOCUMENTS

| | | | |
|---|---|---|---|
| 3,136,766 | 6/1964 | Buc et al. | 260/247.7 |
| 3,155,464 | 11/1964 | Woodruff . | |
| 3,438,757 | 4/1969 | Honnen et al. . | |
| 3,574,576 | 4/1971 | Honnen et al. . | |
| 3,753,670 | 8/1973 | Strange et al. . | |
| 3,756,793 | 9/1973 | Robinson . | |
| 4,155,718 | 5/1979 | Graiff . | |
| 4,160,648 | 7/1979 | Lewis et al. . | |
| 4,191,537 | 3/1980 | Lewis et al. . | |
| 4,198,206 | 4/1980 | Ryan | 23/230 |
| 4,231,759 | 11/1980 | Udelhofen et al. . | |
| 4,236,020 | 11/1980 | Lewis et al. | 560/159 |
| 4,247,301 | 1/1981 | Honnen . | |
| 4,270,930 | 6/1981 | Campbell et al. . | |

(List continued on next page.)

FOREIGN PATENT DOCUMENTS 0330614 8/1989 European Pat. Off. .
106400 7/1973 German Democratic Rep. .

OTHER PUBLICATIONS

Chemical Abstract No. 116:178660s, vol. 116, 1992.

*Primary Examiner*—Prince Willis, Jr.
*Assistant Examiner*—Alan D. Diamond

[57] ABSTRACT

The present invention is directed to the use of cyclic amide alkoxylate compounds as additives in fuel compositions having a major amount of a mixture of hydrocarbons in the gasoline boiling range and a minor amount of one or more cyclic amide alkoxylate compounds of the formula:

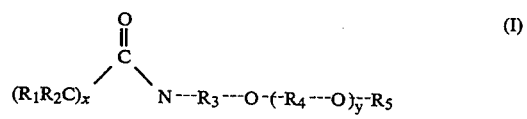

wherein x is from 2 to 20 and y is from 1 to 50. $R_1$ and $R_2$ are independently hydrogen, hydrocarbyl of 1 to 100 carbon atoms or substituted hydrocarbyl of 1 to 100 carbon atoms. $R_3$ is hydrocarbyl of 1 to 100 carbon atoms or substituted hydrocarbyl of 1 to 100 carbon atoms and $R_4$ is independently hydrocarbyl of 2 to 100 carbon atoms or substituted hydrocarbyl of 2 to 100 carbon atoms. $R_5$ is hydrogen, hydrocarbyl of 1 to 100 carbon atoms, or substituted hydrocarbyl of 1 to 100 carbon atoms or acyl of 1 to 20 carbon atoms. The invention is also directed to the use of these cyclic amide alkoxylate compounds for decreasing intake valve deposits, controlling octane requirement increases and reducing octane requirement. The invention is further directed to novel cyclic amide alkoxylate compounds.

83 Claims, No Drawings

U.S. PATENT DOCUMENTS

| | | | |
|---|---|---|---|
| 4,288,612 | 9/1981 | Lewis et al. | 560/159 |
| 4,332,595 | 6/1982 | Herbstman et al. . | |
| 4,397,750 | 8/1983 | Chibnik | 252/51.5 A |
| 4,409,001 | 10/1983 | Sung et al. . | |
| 4,477,261 | 10/1984 | Sung et al. . | |
| 4,486,573 | 12/1984 | Hayashi | 525/285 |
| 4,505,717 | 3/1985 | Sung . | |
| 4,521,330 | 6/1985 | Olstowski et al. | 252/51.5 |
| 4,548,616 | 10/1985 | Sung et al. . | |
| 4,581,040 | 4/1986 | Sung et al. . | |
| 4,604,102 | 8/1986 | Zaweski et al. . | |
| 4,612,335 | 9/1986 | Cuscurida et al. | 521/167 |
| 4,643,737 | 2/1987 | Sung et al. . | |
| 4,643,738 | 2/1987 | Sung et al. . | |
| 4,659,336 | 4/1987 | Sung et al. . | |
| 4,696,755 | 9/1987 | Campbell | 252/515 |
| 4,698,412 | 10/1987 | Tracy et al. | 528/323 |
| 4,747,851 | 5/1988 | Sung et al. . | |
| 4,758,363 | 7/1988 | Sung et al. | 252/51.5 |
| 4,760,152 | 7/1988 | Tracey et al. | 548/551 |
| 4,801,400 | 1/1989 | Login et al. | 252/357 |
| 4,806,609 | 2/1989 | Tracy et al. | 526/264 |
| 4,810,261 | 3/1989 | Sung et al. . | |
| 4,830,851 | 5/1989 | Tracy et al. | 424/78 |
| 4,852,993 | 8/1989 | Sung et al. . | |
| 4,869,728 | 9/1989 | Sung . | |
| 4,881,945 | 11/1989 | Buckley, III . | |
| 4,883,826 | 11/1989 | Marugg et al. | 521/164 |
| 4,936,868 | 6/1990 | Johnson . | |
| 4,958,032 | 9/1990 | O'Lenick, Jr. | 548/543 |
| 4,968,321 | 11/1990 | Sung et al. | 44/337 |
| 4,973,414 | 11/1990 | Nerger et al. | 252/52 |
| 4,975,096 | 12/1990 | Buckley, III | 44/433 |
| 4,975,159 | 12/1990 | Dahms | 205/125 |
| 4,981,493 | 1/1991 | Sung | 44/331 |
| 4,983,384 | 1/1991 | O'Lenick, Jr. | 424/70 |
| 4,985,047 | 1/1991 | Sung et al. | 44/433 |
| 4,992,187 | 2/1991 | Adams et al. | 252/50 |
| 5,028,719 | 7/1991 | O'Lenick, Jr. | 548/544 |
| 5,034,143 | 7/1991 | O'Lenick, Jr. | 252/51.5 |
| 5,061,291 | 10/1991 | Sung | 548/347 |
| 5,123,932 | 6/1992 | Rath et al. | 44/303 |
| 5,141,524 | 8/1992 | Gonzalez | 44/340 |
| 5,147,414 | 9/1992 | Powers, III et al. | 44/347 |

FUEL COMPOSITIONS

BACKGROUND OF THE INVENTION

1. Field of the Invention

The present invention relates to the use of cyclic amide alkoxylate compounds as additives in fuel compositions and the use of these compounds to decrease intake valve deposits, control octane requirement increase, and reduce octane requirement. The present invention further relates to a novel class of cyclic amide alkoxylate compounds.

2. Background

The octane requirement increase effect exhibited by internal combustion engines, e.g., spark ignition engines, is well known in the art. This effect may be described as the tendency for an initially new or relatively clean engine to require higher octane quality fuel as operating time accumulates, and is coincidental with the formation of deposits in the region of the combustion chamber of the engine.

During the initial operation of a new or clean engine, a gradual increase in octane requirement, i.e., fuel octane number required for knock-free operation, is observed with an increasing build up of combustion chamber deposits until a stable or equilibrium octane requirement level is reached. This level appears to correspond to a point in time when the quantity of deposit accumulation on the combustion chamber and valve surfaces no longer increases but remains relatively constant. This so-called "equilibrium value" is normally reached between 3,000 and 20,000 miles or corresponding hours of operation. The actual equilibrium value of this increase can vary with engine design and even with individual engines of the same design; however, in almost all cases, the increase appears to be significant, with octane requirement increase values ranging from about 2 to about 10 research octane numbers being commonly observed in modern engines.

The accumulation of deposits on the intake valves of internal combustion engines also presents problems. The accumulation of such deposits is characterized by overall poor driveability including hard starting, stalls, and stumbles during acceleration and rough engine idle.

Many additives are known which can be added to hydrocarbon fuels to prevent or reduce deposit formation, or remove or modify formed deposits, in the combustion chamber and on adjacent surfaces such as intake valves, ports, and spark plugs, which in turn causes a decrease in octane requirement.

Continued improvements in the design of internal combustion engines, e.g., fuel injection and carburetor engines, bring changes to the environment of such engines thereby creating a continuing need for new additives to control the problem of inlet system deposits and to improve driveability which is usually related to deposits.

It would be an advantage to have fuel compositions which would reduce the formation of deposits and modify existing deposits that are related to octane requirement increase and poor driveability in modern engines which burn hydrocarbon fuels.

SUMMARY OF THE INVENTION

The present invention is directed to the use of cyclic amide alkoxylate compounds as additives in fuel compositions comprising a major amount of a mixture of hydrocarbons in the gasoline boiling range and a minor amount of one or more cyclic amide alkoxylate compounds of the formula:

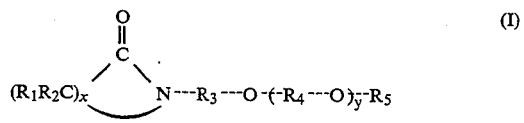
(I)

wherein x is from 2 to 20 and y is from 1 to 50. $R_1$ and $R_2$ are independently hydrogen or hydrocarbyl of 1 to 100 carbon atoms. $R_3$ is hydrocarbyl of 1 to 100 carbon atoms and $R_4$ is independently hydrocarbyl of 2 to 100 carbon atoms. $R_5$ is hydrogen, hydrocarbyl of 1 to 100 carbon atoms or acyl of 1 to 20 carbon atoms.

The invention is also directed to the use of these cyclic amide alkoxylate compounds for decreasing intake valve deposits, controlling octane requirement increases and reducing octane requirement.

The invention is further directed to novel cyclic amide alkoxylate compounds of the formula:

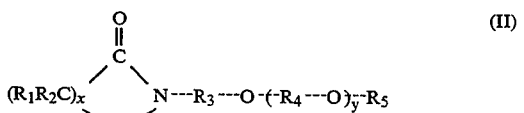
(II)

wherein x is from 2 to 4 and y is from 1 to 50. In such novel compounds, $R_1$ and $R_2$ are independently hydrogen or hydrocarbyl of 1 to 100 carbon atoms, $R_3$ is hydrocarbyl of 1 to 100 carbon atoms and $R_4$ is hydrocarbyl of 2 to 100 carbon atoms with the proviso that when y is greater than 1, each $R_4$ may be the same or different but at least $R_3$ or one $R_4$ must have at least four carbon atoms and $R_5$ is hydrogen, hydrocarbyl of 1 to 100 carbon atoms or acyl of 1 to 20 carbon atoms.

DESCRIPTION OF THE PREFERRED EMBODIMENT COMPOUNDS

The compounds of the present invention, broadly expressed as cyclic amide alkoxylates, are a new class of additives useful for hydrocarbon fuels, e.g., fuels in the gasoline boiling range, for preventing deposits in engines, controlling octane requirement increases and reducing octane requirement, while also decomposing during combustion to environmentally acceptable products. The compounds produce very little residue and are miscible with carriers and other detergents. Non-limiting illustrative embodiments of the compounds useful as additives in the instant invention include those of Formula I:

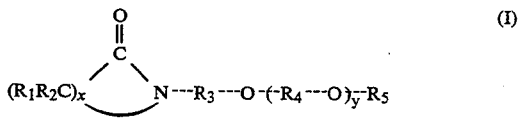
(I)

In Formula I, $R_1$ and $R_2$ are independently hydrogen or hydrocarbyl of 1 to 100 carbon atoms. Preferably, at least one of $R_1$ and $R_2$ is hydrogen. It is even more preferable if both $R_1$ and $R_2$ are hydrogen. As used herein, the term "hydrocarbyl" represents a radical formed by the removal of one or more hydrogen atoms from a carbon atom of a hydrocarbon (not necessarily the same carbon atom). Useful hydrocarbyls are aliphatic, aromatic, substituted, unsubstituted, acyclic or cyclic. Preferably, the hydrocarbyls are aryl, alkyl, alkenyl or cycloalkyl and are straight-chain or branched-chain. Representative hydrocarbyls include methyl, ethyl, butyl, pentyl, methylpentyl, hexenyl, ethylhexyl, dimethylhexyl, octamethylene, octenylene, cyclooctylene, methylcyclooctylene, dimethylcyclooctyl, isooctyl, dodecyl, hexadecenyl, octyl, eicosyl, hexacosyl, triacontyl and phenylethyl. When the hydrocarbyl is substituted, it contains a functional group such as carbonyl, carboxyl, nitro, amino, hydroxy (e.g. hydroxyethyl), oxy, cyano, sulfonyl, and sulfoxyl. The majority of the atoms, other than hydrogen, in substituted hydrocarbyls are carbon, with the heteroatoms (i.e., oxygen, nitrogen, sulfur) representing only a minority, 33% or less, of the total non-hydrogen atoms present.

When $R_1$ and/or $R_2$ are hydrocarbyl, they are each preferably hydrocarbyl of 1 to 20 carbon atoms, even more preferably, alkyl of 1 to 20 carbon atoms and most preferably alkyl of 1 to 8 carbon atoms. When $R_1$ and/or $R_2$ are hydrocarbyl of a relatively high number of carbon atoms, i.e., greater than about 50 carbon atoms, $R_1$ and/or $R_2$ will be represented by polymeric hydrocarbyls such as polyisobutylene, polybutene, polypropylene or polyalpha olefin.

In Formula I, x is from 2 to 20, preferably from 3 to 11. Particularly preferred compounds of Formula I are those in which x is 3, 5 or 11, and especially those compounds in which x is 3.

$R_3$ is hydrocarbyl, as defined hereinbefore, of 1 to 100 carbon atoms, preferably of 1 to 20 carbon atoms. When $R_3$ is hydrocarbyl of a relatively high number of carbon atoms, i.e., greater than about 50 carbon atoms, $R_3$ will be represented by polymeric hydrocarbyls such as polyisobutylene, polybutene, polypropylene or polyalpha olefin. Particularity preferred compounds are those in which $R_3$ is alkyl of 1 to 20 carbon atoms, more preferably when $R_3$ is alkyl of 2 to 10 carbon atoms, and most preferably alkyl of 2 or 4 carbon atoms.

In Formula I, y is from 1 to 50, preferably from 8 to 40, and even more preferably from 18 to 24. Those of ordinary skill in the art will recognize that when the compounds of Formula I are utilized in a composition, y will not have a fixed value but will instead be represented by a range of different values. As used in this specification, y is considered to be a (number) average of the various values of y that are found in a given composition, which number has been rounded to the nearest integer. This is indicated in the various examples by the polydispersity (polydispersity =molecular weight based on the weight average divided by the molecular weight based on the number average).

Each $R_4$ is independently hydrocarbyl, as defined hereinbefore, of 2 to 100 carbon atoms, preferably of 2 to 20 carbon atoms, more preferably of 2 to 14 carbon atoms and most preferably four carbon atoms. When $R_4$ is hydrocarbyl of a relatively high number of carbon atoms, i.e., greater than about 50 carbon atoms, $R_4$ will be represented by polymeric hydrocarbyls such as polyisobutylene, polybutene, polypropylene or polyalpha olefin.

Particularly preferred compounds of Formula I are those in which $R_4$ is hydrocarbyl (geminal or vicinal) of the formula:

wherein $R_6$, $R_7$ and $R_8$ are each independently hydrogen or hydrocarbyl, as defined hereinbefore, of 1 to 98 carbon atoms. Preferred $R_6$, $R_7$ and $R_8$ groups are hydrogen or hydrocarbyl, as defined hereinbefore, of 1 to 18 carbon atoms. $R_7$ and $R_6$, or alternatively $R_6$ and $R_8$, may be taken together to form a divalent linking hydrocarbyl group of 3 to 12 carbon atoms.

The most preferred compounds of Formula I are those in which $R_4$ is hydrocarbyl as represented by Formula III above wherein $R_8$ is hydrogen and $R_6$ is independently hydrogen, alkyl of 1 to 18 carbon atoms or oxy-substituted hydrocarbyl of 1 to 18 carbon atoms, particularly those compounds where $R_8$ is hydrogen and $R_6$ is independently hydrogen or alkyl of 1 to 2 carbon atoms, especially those compounds where $R_8$ is hydrogen and $R_6$ is alkyl of two carbon atoms.

When $R_6$ is oxy-substituted hydrocarbyl of 1 to 18 carbon atoms, $R_6$ is preferably an alkoxy-substituted alkylene of 1 to 18 carbon atoms or an aryloxy-substituted alkylene of 1 to 18 carbon atoms. Particularly preferred alkoxy-substituted alkylene groups include ethylhexyleneoxymethylene, isopropoxymethylene, butoxymethylene and mixtures thereof. Particularly preferred aryl-substituted alkylene groups include nonylphenoxymethylene, phenoxymethylene and mixtures thereof.

When y is greater than 1, the individual $R_4$'s are the same or different. For example, if y is 20, each $R_4$ can be alkyl of four carbon atoms. Alternatively, the $R_4$'s can differ and for instance, independently be alkyl from two to four carbon atoms. When the $R_4$'s differ, they may be present in blocks, i.e., all y groups in which $R_4$ is alkyl of three carbon atoms will be adjacent, followed by all y groups in which $R_4$ is alkyl of two carbon atoms, followed by all y groups in which $R_4$ is alkyl of four carbon atoms. When the $R_4$'s differ, they may also be present in any random distribution.

$R_5$ is hydrogen, hydrocarbyl, as defined hereinbefore, of 1 to 100 carbon atoms or acyl of 1 to 20 carbon atoms. Preferably, $R_5$ is hydrogen. When $R_5$ is hydrocarbyl, it is preferably of 1 to 70 carbon atoms, more preferably of 1 to 20 carbon atoms. The term "acyl", as used herein, represents the residue of an organic acid in which the —OH of a carboxyl group is removed to form $R_9CO$—. $R_9$ is monovalent hydrocarbyl, as defined hereinbefore, of 2 to 19 carbon atoms, preferably, alkyl or aryl of 2 to 19 carbon atoms. Representative acyl groups include acetyl-, butyryl-, caproyl-, acrylyl-, benzoyl- and methacrylyl-. Substituted acyl groups are also contemplated. Substituted acyl groups contain a functional group such as hydroxy, cyano, nitro and the substituents of the hydrocarbyl groups as defined hereinbefore.

Of the compounds of Formula I, the following class of compounds are novel and are defined by the following formula:

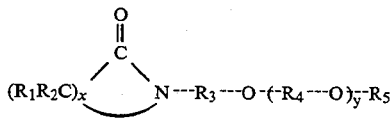

wherein x is from 2 to 4, preferably in which x is 3. $R_1$, $R_2$, $R_3$, $R_4$ and y are as defined hereinbefore with the proviso that when y is greater than 1, at least $R_3$ or one $R_4$ must have at least four carbon atoms. $R_5$ is as defined hereinbefore.

The compounds of Formula I have a weight average molecular weight of at least 600. Preferably, the weight average molecular weight is from about 800 to about 4000, even more preferably from about 1000 to about 2000.

Typical compounds represented by Formula I include those listed by structure in Table 1:

TABLE 1

For the purposes of clarity the hydrogens have been eliminated from the ring structures of Table 1 and the standard shematic structure for a benzene ring (without hydrogen and carbon atoms) has been used.

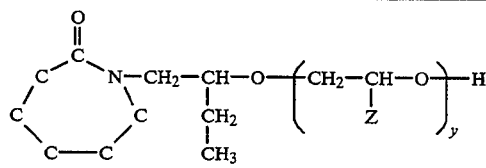

wherein y is from 18 to 24 and Z is independently H, —$CH_3$ or —$CH_2CH_3$ including mixtures thereof.

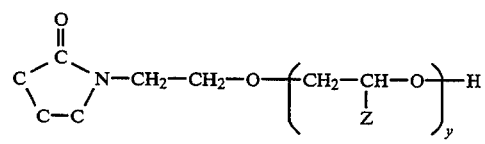

wherein y is from 18 to 24 and Z is independently H, —$CH_3$ or —$CH_2CH_3$ including mixtures thereof.

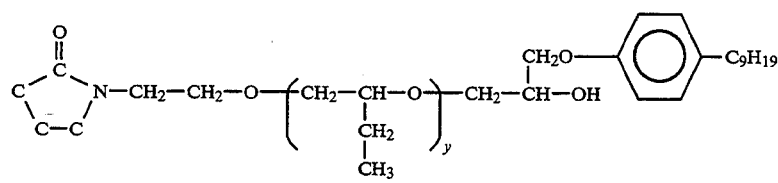

wherein y is from 8 to 40.

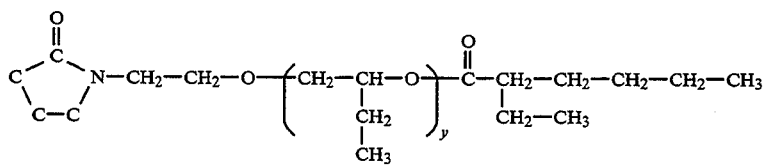

wherein y is from 8 to 40.

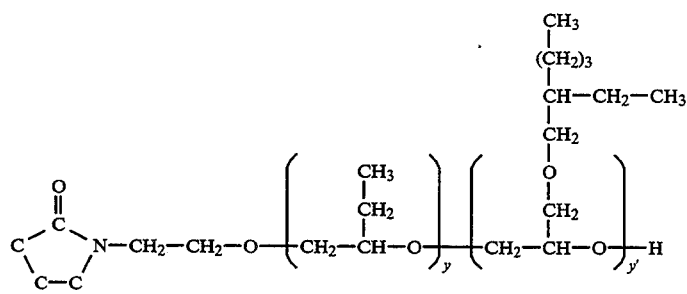

wherein the sum of y and y' is from 1 to 50.

TABLE 1-continued

For the purposes of clarity the hydrogens have been eliminated from the ring structures of Table 1 and the standard shematic structure for a benzene ring (without hydrogen and carbon atoms) has been used.

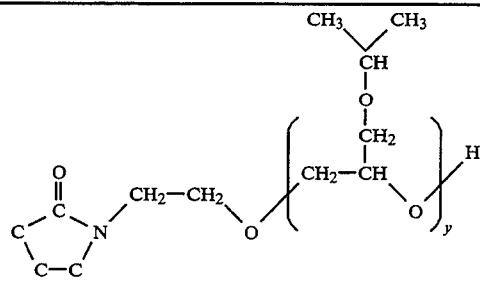

wherein y is from 8 to 40.

The compounds of Formula I are illustratively prepared by alkoxylation, i.e., reacting an initiator selected from cyclic amidoalcohols or cyclic amides with one or more epoxides in the presence of a potassium compound.

In one embodiment, the compounds of Formula I are prepared utilizing cyclic amidoalcohol initiators represented by the general formula:

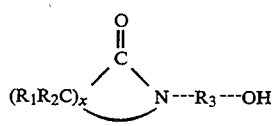

(V)

wherein $R_1$, $R_2$, $R_3$ and x have the above meanings. Non-limiting examples of cyclic amidoalcohol initiators which are employed include N-(2-hydroxyethyl)-pyrrolidinone, N-[2-(2-hydroxyethoxy)ethyl]-pyrrolidinone, N-(2-hydroxypropyl)-pyrrolidinone and N-(2-hydroxy-2-methyl-ethyl)-pyrrolidinone, with N-(2-hydroxyethyl)-pyrrolidinone being the most preferred.

Select cyclic amidoalcohol initiators are available commercially, such as, N-(2-hydroxyethy)-pyrrolidinone (obtained from International Specialty Products or Aldrich Chemical Company). The cyclic amidoalcohol initiators are also prepared by any of the methods known and described in the art, for example by the method of Puetzer et al in J. Am. Chem. Soc. 74 4959 (1952), by reacting a lactone of the formula:

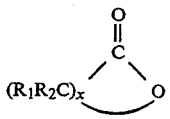

(VI)

with an aminoalcohol of the formula:

$$NH_2-R_3-OH \qquad (VII)$$

wherein $R_1$, $R_2$, and $R_3$ and x have the above meanings. Illustrative lactones for use in making the cyclic amidoalcohols include: α-methyl-γ-butyrolactone, β-methyl-γ-butyrolactone, ε-caprolactone, γ-caprolactone, γ-phenyl-γ-butyrolactone, phthalide, 3,3a,6,6a-tetrahydro-2H-cyclopenta[b]furan-2-one, tetronic acid (tetrahydrofuran-2,6-dione), β-propiolactone and isochromanone. Illustrative aminoalcohols for reacting with lactones to make the cyclic amidoalcohol initiators include: 2-amino-1-butanol, 2-(2-aminoethoxy) ethanol, 2-amino-2-ethyl-1,3-propanediol, 2-amino-2-methyl-1-propanol, 3-amino-1-propanol and 1-amino-2-propanol.

In an alternative embodiment, the compounds of Formula I are prepared by reacting with epoxide the cyclic amide initiators of the general formula:

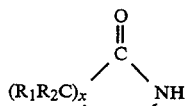

(VIII)

wherein $R_1$, $R_2$ and x have the above meanings. Non-limiting examples of cyclic amides which can be employed include cycloalkyl lactams such as, cyclopropyl lactam, cyclobutyl lactam (butyrolactam), cyclopentyl lactam, cyclohexyl lactam (caprolactam), cycloheptyl lactam and cyclooctyl lactam, with cyclopropyl lactam, cyclobutyl lactam and cyclohexyl lactam being the most preferred.

Select cyclic amide initiators are also available commercially, such as, ε-caprolactam (ε-hexanolactam available commercially from Aldrich Chemical Company), 2-pyrrolidinone (pyrrolidone or γ-butyrolactam available commercially from Aldrich Chemical Company) and laurallactam (2-azacyclotridecanone available commercially from Aldrich Chemical Company) with ε-caprolactam being the most preferred.

The one or more epoxides employed in the reaction with the initiators to prepare the compounds of Formula I contain from 2 to 100 carbon atoms, preferably from 2 to 20 carbon atoms, more preferably from 2 to 14 carbon atoms, and most preferably four carbon atoms. The epoxides may be internal epoxides such as 2,3 epoxides of the formula:

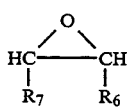

(IX)

wherein $R_6$ and $R_7$ have the above meanings or terminal epoxides such as 1,2 epoxides of the formula:

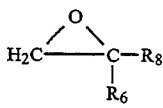

(X)

wherein $R_6$ and $R_8$ have the above meanings. In both Formulas IX and X, $R_7$ and $R_6$, or alternatively $R_6$ and $R_8$, may be taken together to form a cycloalkylene epoxide or a vinylidene epoxide by forming a divalent linking hydrocarbyl group of 3 to 12 carbon atoms.

When $R_6$, $R_7$ and/or $R_8$ are oxy-substituted hydrocarbyl, suitable compounds of Formulas IX and X will include compounds such as nonylphenyl glycidyl ether, phenyl glycidyl ether, cresyl glycidyl ether, butyl glycidyl ether, alkyl $C_{12}$-$C_{13}$ glycidyl ether, alkyl $C_8$-$C_{10}$ glycidyl ether, 2-ethylhexyl glycidyl ether and isopropyl glycidyl ether.

In the preferred embodiment, the terminal epoxides represented by Formula X are utilized to form amido derivatives. Ideally these terminal epoxides are 1,2-epoxyalkanes. Suitable 1,2-epoxyalkanes include 1,2-epoxyethane, 1,2-epoxypropane, 1,2-epoxybutane, 1,2-epoxydecane, 1,2-epoxydodecane, 1,2epoxyhexadecane, 1,2-epoxyoctadecane and mixtures thereof.

In a typical preparation of Formula I compounds, the one or more epoxides and initiator are contacted at a ratio from about 7:1 to about 55:1 moles of epoxide per mole of initiator. Preferably, they are contacted at a molar ratio from about 10:1 to about 30:1, with the most preferred molar ratio being about 20:1.

The reaction is carried out in the presence of potassium compounds which act as alkoxylation catalysts. Such catalysts are conventional and include potassium methoxide, potassium ethoxide, potassium hydroxide, potassium hydride and potassium-t-butoxide. The preferred catalysts are potassium hydroxide and potassium-t-butoxide. The catalysts are used in a base stable solvent such as alcohol, ether or hydrocarbons. The catalysts are employed in a wide variety of concentrations. Generally, the potassium compounds will be used in an amount from about 0.02% to about 5.0% of the total weight of the mixture, preferably from about 0.1% to about 2.0% of the total weight of the mixture, and most preferably about 0.2% of the total weight of the mixture.

The reaction is conveniently carried out in a conventional autoclave reactor equipped with heating and cooling means. The process is practiced batchwise, continuously or semicontinuously.

The manner in which the alkoxylation reaction is conducted is not critical to the invention. Illustratively, the initiator and potassium compound are mixed and heated under vacuum for a period of at least 30 minutes. The one or more epoxides are then added to the resulting mixture, the reactor sealed and pressurized with nitrogen, and the mixture stirred while the temperature is gradually increased.

The temperature for alkoxylation is from about 80° C. to about 250° C., preferably from about 100° C. to about 150° C., and even more preferably from about 120° C. to about 140° C. The alkoxylation reaction time is generally from about 2 to about 20 hours, although longer or shorter times are employed.

Alkoxylation processes of the above type are known and are described, for example in U.S. Pat. No. 4,973,414, U.S. Pat. No. 4,883,826, U.S. Pat. No. 5,123,932 and U.S. Pat No. 4,612,335, each incorporated herein by reference.

The product of Formula I is normally liquid and is recovered by conventional techniques such as filtration and distillation. The product is used in its crude state or is purified, if desired, by conventional techniques such as aqueous extraction, solid absorption and/or vacuum distillation to remove any remaining impurities.

Other methods for making the compounds of Formula I are known by those skilled in the art. For example, the compounds of Formula I are prepared by reacting an initiator as described hereinbefore with other cyclic ethers. In addition, other catalyst chemistry, such as the use of acidic catalysts, can be employed to achieve the compounds of Formula I.

Fuel Compositions

The compounds of Formula I are useful as additives in fuel compositions which are burned or combusted in internal combustion engines. The fuel compositions of the present invention comprise a major amount of a mixture of hydrocarbons in the gasoline boiling range and a minor amount of one or more of the compounds of Formula I. As used herein, the term "minor amount" means less than about 10% by weight of the total fuel composition, preferably less than about 1% by weight of the total fuel composition and more preferably less than about 0.1% by weight of the total fuel composition.

Suitable liquid hydrocarbon fuels of the gasoline boiling range are mixtures of hydrocarbons having a boiling range of from about 25° C. to about 232° C., and comprise mixtures of saturated hydrocarbons, olefinic hydrocarbons and aromatic hydrocarbons. Preferred are gasoline mixtures having a saturated hydrocarbon content ranging from about 40% to about 80% by volume, an olefinic hydrocarbon content from 0% to about 30% by volume and an aromatic hydrocarbon content from about 10% to about 60% by volume. The base fuel is derived from straight run gasoline, polymer gasoline, natural gasoline, dimer and trimerized olefins, synthetically produced aromatic hydrocarbon mixtures, or from catalytically cracked or thermally cracked petroleum stocks, and mixtures of these. The hydrocarbon composition and octane level of the base fuel are not critical. The octane level, $(R+M)/2$, will generally be above about 85.

Any conventional motor fuel base can be employed in the practice of the present invention. For example, hydrocarbons in the gasoline can be replaced by up to a substantial amount of conventional alcohols or ethers, conventionally known for use in fuels. The base fuels are desirably substantially free of water since water could impede a smooth combustion.

Normally, the hydrocarbon fuel mixtures to which the invention is applied are substantially lead-free, but may contain minor amounts of blending agents such as methanol, ethanol, ethyl tertiary butyl ether, methyl tertiary butyl ether, and the like, at from about 0.1% by volume to about 15% by volume of the base fuel, although larger amounts may be utilized. The fuels can also contain conventional additives including antioxidants such as phenolics, e.g., 2,6-di-tert-butylphenol or phenylenediamines, e.g., N,N'-di-sec-butyl-p-phenylenediamine, dyes, metal deactivators, dehazers such as polyester-type ethoxylated alkylphenol-formaldehyde resins. Corrosion inhibitors, such as a polyhydric alcohol ester of a succinic acid derivative having on at least one of its alphacarbon atoms an unsubstituted or substituted aliphatic hydrocarbon group having from 20 to 500 carbon atoms, for example, pentaerythritol diester of polyisobutylene-substituted succinic acid, the polyisobutylene group having an average molecular weight of about 950, in an amount from about 1 ppm by weight to about 1000 ppm by weight, may also be present. The fuels can also contain antiknock compounds such as methyl cyclopentadienylmanganese tricarbonyl and ortho-azidophenol as well as co-antiknock compounds such as benzoyl acetone.

An effective amount of one or more compounds of Formula I are introduced into the combustion zone of the engine in a variety of ways to prevent build-up of deposits, or to accomplish the reduction of intake valve deposits or the modification of existing deposits that are related to octane requirement. As mentioned, a preferred method is to add a minor amount of one or more compounds of Formula I to the fuel. For example, one or more compounds of Formula I are added directly to the fuel or are blended with one or more carriers and/or one or more additional detergents before being added to the fuel.

The amount of cyclic amidoalcohol alkoxylates used will depend on the particular variation of Formula I used, the engine, the fuel, and the presence or absence of carriers and additional detergents. Generally, each compound of Formula I is added in an amount up to about 1000 ppm by weight, especially from about 1 ppm by weight to about 600 ppm by weight based on the total weight of the fuel composition. Preferably, the amount will be from about 50 ppm by weight to about 400 ppm by weight, and even more preferably from about 75 ppm by weight to about 250 ppm by weight based on the total weight of the fuel composition.

The carrier, when utilized, will have a weight average molecular weight from about 500 to about 5000. Suitable carriers, when utilized, include hydrocarbon based materials such as polyisobutylenes (PIB's), polypropylenes (PP's) and polyalphaolefins (PAO's); polyether based materials such as polybutylene oxides (poly BO's), polypropylene oxides (poly PO's), polyhexadecene oxides (poly HO's) and mixtures thereof (i.e., both (poly BO)+(poly PO) and (poly-BO-PO)); and mineral oils such as Exxon Naphthenic 900 sus and high viscosity index (HVI) oils. The carrier is preferably selected from PIB's, poly BO's, and poly PO's, with poly BO's being the most preferred.

The carrier concentration in the final fuel composition is up to about 1000 ppm by weight. When a carrier is present, the preferred concentration is from about 50 ppm by weight to about 400 ppm by weight, based on the total weight of the fuel composition. Once the carrier is blended with one or more compounds of Formula I, the blend is added directly to the fuel or packaged for future use.

The fuel compositions of the present invention may also contain one or more additional detergents. When additional detergents are utilized, the fuel composition will comprise a mixture of a major amount of hydrocarbons in the gasoline boiling range as described hereinbefore, a minor amount of one or more compounds of Formula I as described hereinbefore and a minor amount of an additional detergent selected from polyalkenylamines, Mannich amines, polyalkenyl succinimides, poly(oxyalkylene) carbamates, poly(alkenyl)-N-substituted carbamates and mixtures thereof. As noted above, a carrier as described hereinbefore may also be included. As used herein, the term "minor amount" means less than about 10% by weight of the total fuel composition, preferably less than about 1% by weight of the total fuel composition and more preferably less than about 0.1% by weight of the total fuel composition.

The polyalkylenyl amine detergents utilized comprise at least one monovalent hydrocarbon group having at least 50 carbon atoms and at least one monovalent hydrocarbon group having at most five carbon atoms bound directly to separate nitrogen atoms of a diamine. Preferred polyalkenyl amines are polyisobutenyl amines. Polyisobutenyl amines are known in the art and representative examples are disclosed in various U.S. Pat. Nos. including U.S. Pat. No. 3,753,670, U.S. Pat. No. 3,756,793, U.S. Pat. No. 3,574,576 and U.S. Pat. No. 3,438,757, each incorporated herein by reference. Particularly preferred polyisobutenyl amines for use in the present fuel composition include N-polyisobutenyl-N',N'-dimethyl-1,3-diaminopropane (PIB-DAP) and OGA-472 (a polyisobutenyl ethylene diamine available commercially from Oronite).

The Mannich amine detergents utilized comprise a condensation product of a high molecular weight alkyl-substituted hydroxyaromatic compound, an amine which contains an amino group having at least one active hydrogen atom (preferably a polyamine), and an aldehyde. Such Mannich amines are known in the art and are disclosed in U.S. Pat. No. 4,231,759, incorporated herein by reference. Preferably, the Mannich amine is an alkyl substituted Mannich amine.

The polyalkenyl succinimides detergents comprise the reaction product of a dibasic acid anhydride with either a polyoxyalkylene diamine, a hydrocarbyl polyamine or mixtures of both. Typically the succinimides is substituted with the polyalkenyl group but the polyalkenyl group may be found on the polyoxyalkylene diamine or the hydrocarbyl polyamine. Polyalkenyl succinimides are also known in the art and representative examples are disclosed in various U.S. Pat. Nos. including U.S. Pat. No. 4,810,261, U.S. Pat. No. 4,852,993, U.S. Pat. No. 4,968,321, U.S. Pat. No.4,985,047, U.S. Pat. No. 5,061,291 and U.S. Pat. No. 5,147,414, each incorporated herein by reference.

The poly(oxyalkylene) carbamate detergents comprise an amine moiety and a poly(oxyalkylene) moiety linked together through a carbamate linkage, i.e., $$—O—C(O)—N— \qquad (XI)$$

These poly(oxyalkylene) carbamates are known in the art and representative examples are disclosed in various U.S. Pat. Nos. including, U.S. Pat. No. 4,191,537, U.S. Pat. No. 4,160,648, U.S. Pat. No. 4,236,020, U.S. Pat. No. 4,270,930, U.S. Pat. No. 4,288,612 and U.S. Pat. No. 4,881,945, each incorporated herein by reference. Particularly preferred poly (oxyalkylene) carbamates for use in the present fuel composition include OGA-480 (a poly(oxyalkylene) carbamate which is available commercially from Oronite).

The poly(alkenyl)-N-substituted carbamate detergents utilized are of the formula:

$$R—A—\overset{\overset{\displaystyle O}{\|}}{C}—OR^1 \qquad (XII)$$

in which R is a poly(alkenyl) chain; $R^1$ is a hydrocarbyl or substituted hydrocarbyl group; and A is an N-substituted amino group. Poly(alkenyl)-N-substituted carbamates are known in the art and are disclosed in U.S. Pat. No. 4,936,868, incorporated herein by reference.

The one or more additional detergents are added directly to the hydrocarbons, blended with one or more carriers, blended with one or more compounds of Formula I, or blended with one or more compounds of Formula I and one or more carriers before being added to the hydrocarbons.

The concentration of the one or more additional detergents in the final fuel composition is generally up to about 1000 ppm by weight for each additional detergent. When one or more additional detergents are utilized, the preferred concentration for each additional detergent is from about 50 ppm by weight to about 400 ppm by weight, based on the total weight of the fuel composition, even more preferably from about 75 ppm by weight to about 250 ppm by weight, based on the total weight of the fuel composition.

Engine Tests

Decreasing Intake Valve Deposits

The invention further provides a process for decreasing intake valve deposits in engines utilizing the cyclic amide alkoxylates of the present invention. The process comprises supplying to and combusting or burning in an internal combustion engine a fuel composition comprising a major amount of hydrocarbons in the gasoline boiling range and a minor amount of one or more compounds of Formula I as described hereinbefore.

By supplying to and combusting or burning the fuel composition in an internal combustion engine, deposits in the induction system, particularly deposits on the tulips of the intake valves, are reduced. The reduction is determined by running an engine with clean induction system components and pre-weighed intake valves on dynamometer test stands in such a way as to simulate road operation using a variety of cycles at varying speeds while carefully controlling specific operating parameters. The tests are run for a specific period of time on the fuel composition to be tested. Upon completion of the test, the induction system deposits are visually rated, the valves are reweighed and the weight of the valve deposits is determined.

Controlling Octane Requirement Increases

The invention further provides a process for controlling octane requirement increases in engines utilizing the cyclic amide alkoxylates of the present invention. The process comprises supplying to and combusting or burning in an internal combustion engine a fuel composition comprising a major amount of hydrocarbons in the gasoline boiling range and a minor amount of one or more compounds of Formula I as described hereinbefore.

Octane requirement is the maximum octane number of a gasoline that presents trace knock in a given engine within the engine's normal operating range. An increase in octane requirement is generally experienced during mileage accumulation on a new engine. The increase is typically attributed to an increase in engine deposits. Octane requirement increase control is a performance feature that is usually expressed as a comparison of the octane requirement increase developed with a gasoline containing additives (test gasoline) relative to a version of the same gasoline without additives (base gasoline), i.e., the positive difference obtained by subtracting the results of gasoline containing additives from gasoline which does not contain additives.

The test protocol for octane requirement increase control must establish the stable octane requirement of the base gasoline relative to a clean engine. Base gasoline is typically the test gasoline without additives or special treatment; however, it may be gasoline containing additives for a specific comparison.

Octane requirement increase control testing consists of operating an engine assembled with clean combustion chambers and induction system components on a test gasoline to octane stabilization, measuring the octane requirement at regular intervals. The octane requirement increase control is the difference between the stabilized octane requirement of the engine operated on test gasoline and that of the stabilized octane requirement of the engine on base gasoline.

Reduction of Octane Requirement

The invention still further provides a process for reducing octane requirement in engines utilizing the cyclic amide alkoxylates of the present invention. The process comprises supplying to and combusting or burning in an internal combustion engine a fuel composition comprising a major amount of hydrocarbons in the gasoline boiling range and a minor amount of one or more compounds of Formula I as described hereinbefore.

Octane requirement reduction is the reduction of the octane requirement of an engine by the action of a particular gasoline, usually measured as a decrease from a stabilized octane requirement condition.

Octane requirement reduction is a performance feature that demonstrates a reduction from the established octane requirement of a base gasoline in a given engine. Octane requirement reduction testing consists of operating an engine, which has achieved stable octane requirement using base gasoline, on a test gasoline for approximately 100 hours. Octane measurements are made daily and octane requirement reduction is a reduction of octane requirement from that of base gasoline. Several octane requirement reduction tests may be conducted in a series for fuel to fuel comparison, or test fuel to base fuel comparison, by restabilizing on base fuel between octane requirement reduction tests.

The contribution of specific deposits is determined by removing deposits of interest and remeasuring octane requirement immediately after the engine is warmed to operating temperature. The octane requirement contribution of the deposit is the difference in ratings before and after deposit removal.

The ranges and limitations provided in the instant specification and claims are those which are believed to particularly point out and distinctly claim the instant invention. It is, however, understood that other ranges and limitations that perform substantially the same function in substantially the same way to obtain the same or substantially the same result are intended to be within the scope of the instant invention as defined by the instant specification and claims.

The invention will be described by the following examples which are provided for illustrative purposes and are not to be construed as limiting the invention.

EXAMPLES

Compound Preparation

The cyclic amide alkoxylates used in the following examples were prepared by reacting an initiator with one or more epoxides in the presence of a potassium compound to produce compounds of Formula I (or Formula II) having a weight average molecular weight from about 600 to about 4000 as measured by gel permeation chromatography (GPC), nuclear magnetic resonance (NMR), infrared spectroscopy (IR), elemental analysis or nitrogen/amine analysis.

EXAMPLE 1

A mixture of N-(2-hydroxyethyl)-pyrrolidinone (52 g, 0.40 moles), potassium hydroxide (1.9 g in 1.5 g water) and toluene (200 g) was heated to approximately 80° C. under reduced pressure of 10 mm Hg for over 30 minutes. The mixture was added along with 1,2-epoxybutane (598 g, 8.3 moles) to a one liter autoclave equipped with heating and cooling means. The autoclave was sealed and purged of air by pressurizing and depressurizing with nitrogen at 50 psi several times. With stirring and an initial nitrogen pressure of 50 psi, the mixture was heated slowly to 120° C. and held at this temperature for over 12 hours. During the process, a maximum autogenous pressure at 125 psi at 127° C. was observed. The pressure had dropped to 63 psi by the end of the reaction. The mixture was then cooled to ambient temperature, excess gas was vented and the product was recovered as a light brown liquid. This crude product was rotovapped at 80° C. and 10 mm Hg to remove light material. Approximately 1.0 g of 1,2-epoxybutane was removed, indicating nearly quantitative conversion of the 1,2-epoxybutane.

GPC, NMR and IR analysis were consistent with the desired structure of a N-(2-hydroxyethyl)-pyrrolidinone butoxylate at approximately 20 units of 1,2-epoxybutane adduct.

The crude product was further purified using an extraction procedure to remove trace amounts of color body. The crude product was dissolved in hexane (50% basis of product) and extracted utilizing water three times at ambient temperature. The organic layer was then subjected to rotovap at 80° C. and 10 mm Hg to obtain a final product having an estimated molecular weight of approximately 1600. GPC analysis indicated an average molecular weight of Mw=1250 and a polydispersity of 1.08.

EXAMPLE 2

The procedure of Example 1 was repeated with the following exceptions: a mixture of N-(2-hydroxyethyl)-pyrrolidinone (48g, 0.37 moles) and potassium hydroxide (1.7g in 1.7g water) was utilized in the absence of toluene. The mixture was added along with a mixture of 1,2-epoxybutane (442 g, 6.1 moles) and nonylphenol epoxide (110 g, 0.40 moles, an epoxy marketed as HELOXY 64 by Rhone-Poulenc, with a structure derived from nonylphenol and epichlorohydrin) to the autoclave. The mixture was heated slowly to 118° C. and maintained at this temperature for over 8 hours.

The product was confirmed by GPC, NMR and IR analysis. The crude product was further purified by the procedure of Example 1 to give a final product having an estimated molecular weight of approximately 1600. GPC analysis indicated an average molecular weight of Mw=1100 and a polydispersity of 1.12.

EXAMPLE 3

The procedure of Example 1 was repeated with the following exceptions: a mixture of N-(2-hydroxyethyl)-pyrrolidinone (HEP) (43.3 g, 0.34 moles) and potassium hydroxide (1.7 g in 1.7 g water) was utilized in the absence of toluene. The resulting mixture was added along with propylene oxide (498 g, 8.6 moles) to the autoclave. The mixture was heated slowly to from 117° C. to 120° C. and maintained at this temperature for over 6 hours.

NMR analysis indicated a 71% yield of a HEP propoxylate having an average of 25 propylene oxide adducts. The crude product was further purified by the procedure of Example 1 to give a final product having an estimated molecular weight of approximately 1600. GPC analysis indicated an average molecular weight of Mw=1260 and a polydispersity of 1.11.

EXAMPLE 4

The procedure of Example 1 was repeated with the exception that the crude product was further purified using a filtration procedure. The crude product was mixed with disodium dihydrogen pyrophosphate ($Na_2H_2P_2O_7$, 1.25 molar ratio to potassium) and water (5% wt basis of product). The mixture was heated to 80° C. for over one hour with agitation. The slurry was filtered to remove solid material and to obtain a light-colored liquid as the final product containing less than 30 ppm by weight potassium and sodium.

EXAMPLE 5

The procedure of Example 1 was repeated with the following exceptions: a mixture of N-(2-hydroxyethyl)-pyrrolidinone (40 g, 0.31 moles) and potassium hydride (1.2 g) were mixed for over 30 minutes at ambient temperature. No toluene was used. The resulting liquid was added along with 1,2-epoxybutane (561 g, 7.8 moles) to the autoclave. The autoclave was sealed and purged of air and filled with nitrogen to 200 psi while still at ambient temperature. The mixture was heated slowly to 137° C. and maintained at this temperature for over 6 hours. During the process, a maximum autogenous pressure at 319 psi at 137° C. was observed. The pressure dropped to 271 psi at the end of the reaction.

The crude product was purified using an extraction procedure in which the crude product was dissolved in hexane (50% basis of product) before being extracted three times with a mixture of methanol/ethanol/water at a ratio of approximately 1:0.2:1. The product was then subjected to rotovap at 80° C. and 10 mm Hg to obtain a light-colored (yellow) transparent fluid. A final product having an estimated molecular weight of approximately 2000 was obtained. GPC analysis indicated an average molecular weight of Mw=1440 and a polydispersity of 1.09.

EXAMPLE 6

The procedure of Example 1 was repeated with the following exceptions: a mixture of N-(2-hydroxyethyl)-pyrrolidinone (59.5 g, 0.46 moles) and potassium hydroxide (1.7 g in 1.7 g water) was utilized in the absence of toluene. The resulting mixture was added along with 1,2-epoxybutane (540 g, 7.5 moles) to the autoclave. The mixture was heated slowly to 118° C. and maintained at this temperature for over 7 hours. During the process, a maximum autogenous pressure at 125 psi at 120° C. was observed.

The crude product was purified by the procedure of Example 1 to give a final product having an estimated molecular weight of approximately 1300. GPC analysis indicated an average molecular weight of Mw=1060 and a polydispersity of 1.08.

EXAMPLE 7

The procedure of Example 1 was repeated with the following exceptions: a mixture of N-(2-hydroxyethyl)-pyrrolidinone (97 g, 0.75 moles), potassium hydroxide (1.4 g) and toluene (50 g) was stirred at ambient temperature under nitrogen atmosphere until dissolved. The mixture was subjected to rotary evaporation under reduced pressure (10mm Hg) and heat (80° C.) to remove water. The resulting liquid was added along with 1,2-epoxybutane (503 g, 7.0 moles) to the autoclave. The pressure was increased to 200 psi and while stirring, the mixture was heated slowly to between 137° C. and 140° C. and held at this temperature for over 7 hours. During the process, a maximum autogenous pressure at 370 psi was observed.

The crude product was purified by the procedure of Example 1 to give a final product having an estimated molecular weight of approximately 800. GPC analysis indicated an average molecular weight of Mw=746 and a polydispersity of 1.05.

EXAMPLE 8

The procedure of Example 1 was repeated with the following exceptions: a mixture of 2-pyrrolidinone (32g, 0.38 moles) and potassium t-butoxide (1.7g) was utilized in the absence of toluene. The resulting material was added with 1,2-epoxybutane (568g, 7.9 moles) to the autoclave. The mixture was heated slowly to a temperature from 137° C. to 141° C. for over 7 hours. A pressure of from about 370 psi to about 278 psi was recorded during this time. The final product had an estimated molecular weight of approximately 1600. GPC analysis indicated an average molecular weight of Mw=1240 and a polydispersity of 1.08.

EXAMPLE 9

The procedure of Example 1 was repeated with the following exceptions: a mixture of ε-caprolactam (42.4g, 0.375 moles), potassium hydroxide (1.9g in 1.5 g water) and toluene (100g) was utilized. This mixture was added along with 1,2-epoxybutane (558g, 7.75 moles) to the autoclave. The mixture was slowly heated to from 118° C. to 119° C. under nitrogen pressure (73 psi to 123 psi) for over 6 hours. The crude product was purified by the procedure of Example 1 to give a final product having an estimated molecular weight of approximately 1600. GPC analysis indicted an average molecular weight of Mw=1230 and a polydispersity of 1.09.

EXAMPLE 10

A mixture of N-(2-hydroxyethyl)-pyrrolidinone (HEP) (129 g, 1.0 moles) and potassium t-butoxide (0.5 g) was heated to approximately 80° C. under a reduced pressure of 10 mm Hg for 30 minutes. The mixture was placed in a one liter autoclave, and the air was replaced with nitrogen. The reactor contents were pressured to 30 psig of nitrogen and heated to 150° C. Ethylene oxide (EO)(132 g, 3.0 moles) was fed slowly at 60 psig to the mixture over a 45 minute period. After the ethylene oxide was added, the mixture was maintained at 150° C. for an additional 30 minutes to complete the reaction. The reaction was cooled to ambient temperature without neutralization and the ethoxylate adduct was isolated.

A portion of the ethoxylated adduct (52 g, 0.2 moles) was dissolved in butylene oxide (BO)(288 g, 4.0 moles) at 25° C. and added to the autoclave. The autoclave was sealed, purged of air and pressurized to 50 psig using nitrogen. The system was heated to 140° C., producing a total pressure of 140 psig and maintained at this temperature for 5 hours. The reaction mixture was cooled to 25° C. and the crude yellow product was rotovapped at 80° C. and 10 mm Hg to remove any light material. A total of 330 grams was isolated. The product was purified by aqueous extraction as described in Example 1. The product was of the general formula $HEP(EO)_3(BO)_{20}H$ with an estimated molecular weight of approximately 1800.

EXAMPLE 11

An ethoxylate adduct was produced according to the procedure of Example 10 using N-(2-hydroxyethyl)-pyrrolidinone (103.2 g, 0.8 moles), potassium-t-butoxide (0.7 g) and ethylene oxide (246.4 g, 5.6 moles). The product was isolated unneutralized.

A portion of this ethoxylated adduct (87.4 g, 0.2 moles) was reacted with butylene oxide (245 g, 3.4 moles) according to the procedure of Example 10. The product was isolated and purified by aqueous extraction as described in Example 1. The product was of the general formula $HEP(EO)_7(BO)_{17}H$ with an estimated molecular weight of approximately 1800.

EXAMPLE 12

A mixture of N-(2-hydroxyethyl)-pyrrolidinone (23.2 g, 0.18 moles), potassium butoxide (1.0 g) and propylene oxide (301 g, 5.19 moles) was placed in an autoclave and pressurized to 200 psig using nitrogen. The contents were allowed to react at 120° C. for 9 hours. The pressure decreased from 395 psig to 250 psig over the course of the reaction. The reaction mixture was cooled, and the yellow product purified by aqueous extraction as described in Example 1. The estimated molecular weight of the product was approximately 1800.

EXAMPLE 13

A mixture of N-(2-hydroxyethyl)-pyrrolidinone (23.2 g, 0.18 moles), potassium t-butoxide (1.0 g), propylene oxide (136 g, 2.34 moles) and 2-ethylhexyl glycidyl ether (obtained from Aldrich Chemical Company, 167 g, 0.9 moles) were reacted according to the procedure of Example 1. The final product was also purified by aqueous extraction as described in Example 1. The estimated molecular weight of the product was approximately 1800.

EXAMPLE 14

A mixture of N-(2-hydroxyethyl)-pyrrolidinone (21.9 g, 0.17 moles), potassium t-butoxide (1.0 g) and 2-ethylhexyl glycidyl ether (234 g, 1.53 moles) was reacted according to the procedure of Example 1. The final product was purified by aqueous extraction as described in Example 1 to obtain a product having an estimated molecular weight of approximately 1800.

EXAMPLE 15

A mixture of N-(2-hydroxyethyl)-pyrrolidinone (21.9 g, 0.17 moles), potassium t-butoxide (1.0 g), butylene oxide (142 g, 1.97 moles) and 2-ethylhexyl glycidyl ether (142 g, 0,765 moles) were reacted according to the procedure of Example 1. The product was purified by aqueous extraction as described in Example 1 to obtain a product having an estimated molecular weight of approximately 1800.

EXAMPLE 16

A mixture of N-(2-hydroxyethyl)-pyrrolidinone (23.2 g, 0.18 moles), potassium t-butoxide (1.0 g) and isopropyl glycidyl ether (obtained from Aldrich Chemical Company, 301 g, 2.58 moles) was reacted according to the procedure of Example 1. The product was purified by aqueous extraction as described in Example 1 to obtain a product having an estimated molecular weight of approximately 1800.

EXAMPLE 17

600 g (0.375 moles) of the product of Example 1 was placed in a one liter, 3-necked round-bottomed flask equipped with a mechanical stirrer, temperature controller, Dean-stark trap and water condenser. Under nitrogen atmosphere, 2-ethylhexanoic acid (54 g, 0.375 moles) was added. While stirring under nitrogen flow, the mixture was heated to from about 130° C. to about 180° C. for over 10 hours. Some light boiling materials (13 ml) were removed through the trap. The resulting material (an esterification product) was further purified by extraction with water and rotovapped under 80° C., 10 mm Hg vacuum. GPC analysis indicated a similar molecular weight and distribution to the compound of Example 1 but with a slightly broader polydispersity (1.12 vs. 1.09).

EXAMPLE 18

The procedure of Example 1 was repeated with the exception that 300g (4.16 moles) of 1,2-epoxybutane was utilized to obtain a product having an estimated molecular weight of 1800.

Test Results

In each of the following tests, the base fuel utilized comprised either premium unleaded gasoline (PU) (90+ octane, [R+M/2]) and/or regular unleaded gasoline (RU) (85–88 octane, [R+M/2]). Those skilled in the art will recognize that fuels containing heavy catalytically cracked stocks, such as most regular fuels, are typically more difficult to additize in order to control deposits and effectuate octane requirement reduction and octane requirement increase control. The cyclic amide alkoxylate compounds utilized were prepared as indicated by Example number and were used at the concentration indicated in ppm by weight. The tests employed are described below and the results of the various tests are set forth in the tables below.

Intake Valve Deposit Tests

Engines from vehicles were installed in dynamometer cells in such a way as to simulate road operation using a cycle of idle, low speed and high speed components while carefully controlling specific operating parameters. Fuels with and without the compounds of Formula I were tested in a variety of engines having port fuel injection including, 2.3 L Fords, 2.3 L Oldsmobiles (Olds), 3.3 L Dodges, 3.1 L Chevrolets (Chev) and 2.7 L BMWs to determine the effectiveness of the instant compounds in reducing intake valve deposits ("L" refers to liter). Carbureted 0.359 L Honda generator engines were also utilized to determine the effectiveness of the instant compounds in reducing intake valve deposits.

Before each test, the engine was inspected, the induction system components were cleaned and new intake valves were weighed and installed. The oil was changed and new oil and fuel filters, gaskets and spark plugs were installed.

In all engines except the Honda, the tests were run in cycles consisting of idle, 35 mph and 65 mph for a period of 100 hours unless indicated otherwise. In the Honda engines, the tests were run in cycles consisting of a no load idle mode for one minute followed by a three minute mode with a load at 2200 rpm's for a period of 40 hours unless indicated otherwise. At the end of each test, the intake valves were removed and weighted.

TABLE 2

Intake Valve Deposits in Honda Generator Engines

| Compound Example # | Fuel | Conc. ppm by Weight | Average Deposit Weight, mg |
|---|---|---|---|
| 1 | PU | 200 | 10.5* |
| — | PU | 0 | 25.1* |
| 1 | PU | 200 | 16, 10 |
| 2 | PU | 200 | 5 |
| 3 | PU | 200 | 17 |
| 7 | PU | 200 | 23 |
| 9 | PU | 200 | 12 |
| — | PU | 0 | 39 |
| 6 | PU | 200 | 27 |
| — | PU | 0 | 83, 79 |
| 1 | RU | 200 | 39 |
| 1 | RU | 300 | 34 |
| 2 | RU | 200 | 34 |
| — | RU | 0 | 98 |

*Indicates an average of five tests in three different Honda generator engines.

Results of these tests demonstrate that the compounds of the present invention are very useful in significantly preventing the accumulation of deposits on the intake valves in the generator engines tested as compared to the effects of the base fuel (indicated by no compound example # and 0 ppm by weight) as shown by the much lower average valve deposits.

TABLE 3

Intake Valve Deposits in Various Engines

| Compound Example # | Engine | Fuel | Conc. ppm by Weight | Average Deposit Weight, mg |
|---|---|---|---|---|
| — | 2.8 L Chev | PU | 0 | 232* |
| 1 | " | PU | 100 | 297 |
| 1 | " | PU | 200 | 212 |
| 1 | " | PU | 300 | 232 |
| 1 | " | PU | 400 | 55 |
| — | 2.3 L Olds | PU | 0 | 174* |
| 1 | " | PU | 200 | 56 |
| 1 | " | PU | 300 | 67 |
| — | 3.3 L Dodge | PU | 0 | 211 |
| 1 | " | PU | 200 | 176 |
| 9 | " | PU | 200 | 28 |
| 4 | " | PU | 200 | 132 |
| 8 | " | PU | 200 | 77 |
| 9 | " | PU | 200 | 28 |
| — | 3.1 L Chev | PU | 0 | 72 |
| 1 | " | PU | 200 | 38, 69 |
| 1 | " | PU | 300 | 115 |
| 9 | " | PU | 200 | 33 |
| — | " | RU | 0 | 143 |
| 1 | " | RU | 200 | 470 |
| 9 | " | RU | 200 | 235 |
| — | 2.7 L BMW | PU | 0 | 138* |

TABLE 3-continued

Intake Valve Deposits in Various Engines

| Compound Example # | Engine | Fuel | Conc. ppm by Weight | Average Deposit Weight, mg |
|---|---|---|---|---|
| 1 | " | PU | 200 | 86 |
| 4 | " | PU | 200 | 123 |
| 5 | " | PU | 200 | 115 |
| — | 2.3 L Ford | PU | 0 | 242 |
| 1 | " | PU | 200 | 59 |
| 2 | " | PU | 200 | 122 |
| 9 | " | PU | 200 | 50 |
| — | " | RU | 0 | 243 |
| 1 | " | RU | 200 | 193 |
| 9 | " | RU | 200 | 194 |
| 2 | " | RU | 200 | 242 |
| 17 | " | RU | 200 | 388 |

*Indicates that base fuel having a different blend but the same octane was utilized.

Results of these tests demonstrate that the compounds of the present invention are very useful in significantly preventing the accumulation of deposits on the intake valves in the majority of the engines tested as compared to the effects of the base fuel (indicated by no compound example # and 0 ppm by weight) as shown by the lower average valve deposits.

TABLE 4

Intake Valve Deposit Tests Utilizing Additional Detergents and Carrier Fluids
Additional intake valve deposit tests (as defined hereinbefore) were conducted in the 2.7 L BMWi utilizing compounds as prepared in Example 1 and additional components (detergents or carrier fluids) in regular unleaded gasoline.

| Conc. ppm by Weight of Example 1 | Conc. ppm by Weight of Additional Component | Average Deposit Weight, mg |
|---|---|---|
| 0 | 0 | 185 |
| 200 | 50 ppm OGA-480[1] | 219 |
| 200 | 50 ppm PIB-DAP[2] | 233 |
| 125 | 125 ppm PIB-DAP[2] | 32 |
| 150 | 300 ppm PIB[3] | 115 |
| 150 | 300 ppm PAO[5] | 189 |
| 200 | 250 ppm PPO[5] | 199 |

TABLE 4-continued

Intake Valve Deposit Tests Utilizing Additional Detergents and Carrier Fluids
Additional intake valve deposit tests (as defined hereinbefore) were conducted in the 2.7 L BMWi utilizing compounds as prepared in Example 1 and additional components (detergents or carrier fluids) in regular unleaded gasoline.

| Conc. ppm by Weight of Example 1 | Conc. ppm by Weight of Additional Component | Average Deposit Weight, mg |
|---|---|---|
| 125 | 125 ppm MA[6] | 5 |

[1]OGA-480 -a poly(oxyalkylene) carbamate available commercially from Oronite.
[2]PIB-DAP - N-polyisobutenyl-N',N'-dimethyl-1,3-diaminopropane, Mw = 1050
[3]PIB - polyisobutylene, Mw = 750.
[4]PAO (8 cst) - polyalpha olefins (8 cst).
[5]PPO - Polypropylene oxide, MW = 1600.
[6]MA - an alkyl substituted Mannich amine also known as Amoco 595, commercially available from Ethyl Additives.

Results of these tests demonstrate that the compounds of the present invention, when combined with carrier fluids or additional detergents are useful in preventing the accumulation of deposits on intake valves.

TABLE 5

Intake Valve Deposit Tests Utilizino Additional Detergents and Carrier Fluids
Additional intake valve deposit tests (as defined hereinbefore) were conducted in the 0.359 L Honda generator engine utilizing compounds as prepared in Example 1 and additional components (detergents or carrier fluids) in regular unleaded gasoline.

| Conc. ppm by weight of Example 1 | Conc. ppm by weight of Additional Component | Average Deposit Weight, mg | CC Dpst Wt (mg) |
|---|---|---|---|
| 125 | 0 | 49.0 | 1133 |
| 125 | 125 ppm PIB-DAP[1] | 0.4 | 1492 |
| 125 | 125 ppm MPDC[2] | 29.3 | 1520 |
| 125 | 300 ppm EN-900[3] | 29.4 | — |

[1]PIB-DAP - N-polyisobutenyl-N',N'-dimethyl-1,3-diaminopropane, Mw = 1050.
[2]MPDC - Methyl Pib-Dap Carbamate, Mw = 1100.
[3]EN-900 - Exxon Naphthenic 900 sus.

Results of these tests further demonstrate that the compounds of the present invention, when combined with carrier fluids or co-detergents are useful in preventing the accumulation of deposits on intake valves.

TABLE 6

Honda Generator Engine Test Results Using Various Alkylene Oxide Adducts of HEP
Additional intake valve deposit tests (as defined hereinbefore) were conducted in 0.359 L Honda generator engines in premium unleaded gasoline using a variety of alkylene oxide adducts of N-(2-hydroxyethyl)-pyrrolidinone (HEP). The various derivatives constitute variations of the polyether backbone in one of three ways:
  a) mixtures of ethylene oxide (EO)/butylene oxide (BO)
  b) mixtures of propylene oxide (PO)/other alkylene oxides
  c) other pure alkylene oxides.
For purposes of clarity the hydrogens have been eliminated from the ring structures of Table 6. Example 1 was included for comparison. All compounds have an estimated molecular weight of approximately 1800 and were used at 200 ppm by weight concentrations.

| Compound Example | Chemical Description | Structure | Average Deposit |
|---|---|---|---|
| 18* | HEP(BO)$_{24}$H | 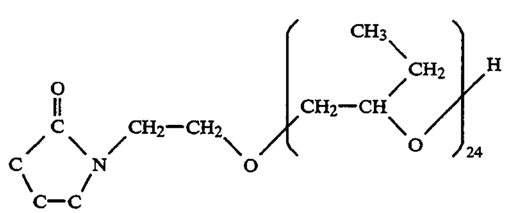 | 12.2 |

TABLE 6-continued

| # | Name | Structure | Value |
|---|---|---|---|
| 10* | HEP(EO)$_3$(BO)$_{20}$H | pyrrolidinone-N-CH$_2$CH$_2$O-(CH$_2$CH$_2$O)$_3$-(CH$_2$CH(CH$_2$CH$_3$)O)$_{20}$-H | 13.9 |
| 11* | HEP(EO)$_7$(BO)$_{17}$H | pyrrolidinone-N-CH$_2$CH$_2$O-(CH$_2$CH$_2$O)$_7$-(CH$_2$CH(CH$_2$CH$_3$)O)$_{17}$-H | 14.9 |
| 12 | HEP(PO)$_{29}$H | pyrrolidinone-N-CH$_2$CH$_2$O-(CH$_2$CH(CH$_3$)O)$_{29}$-H | 18.7 |
| 13 | HEP(PO)$_{14}$(EHGE)$_5$H | pyrrolidinone-N-CH$_2$CH$_2$O-(CH$_2$CH(CH$_3$)O)$_{14}$-(CH$_2$CH(CH$_2$OCH$_2$CH(CH$_2$CH$_3$)(CH$_2$)$_3$CH$_3$)O)$_5$-H | 26.5 |
| 18 | HEP(BO)$_{24}$H | pyrrolidinone-N-CH$_2$CH$_2$O-(CH$_2$CH(CH$_2$CH$_3$)O)$_{24}$-H | 7.9 |
| 14 | HEP(EHGE)$_9$H | pyrrolidinone-N-CH$_2$CH$_2$O-(CH$_2$CH(CH$_2$OCH$_2$CH(CH$_2$CH$_3$)(CH$_2$)$_3$CH$_3$)O)$_9$-H | 18.1 |

TABLE 6-continued

| | | | |
|---|---|---|---|
| 15 | HEP(BO)$_{11}$(EHGE)$_5$H | [structure: HEP-CH$_2$-CH$_2$-O-[CH$_2$-CH(CH$_3$)-O]$_{11}$-[CH$_2$-CH(O-CH$_2$-CH(CH$_2$-CH$_3$)-(CH$_2$)$_3$-CH$_3$)]$_5$-H] | 12.6 |
| 16 | HEP(GIE)$_{14}$H | [structure: HEP-CH$_2$-CH$_2$-O-[CH$_2$-CH(O-CH$_2$-CH(CH$_3$)$_2$)-O]$_{14}$-H] | 22.6 |

*Indicates that a different Honda generator engine was used as compared to those test runs without an asterisk.
The following abbreviations were used throughout Table 6:
HEP = n-(2-hydroxyethyl)-pyrrolidinone
BO = butylene oxide
EO = ethylene oxide
PO = propylene oxide
EHGE = ethylhexyl glycidyl ether
GIE = glycidyl isopropyl ether
The results of Table 6 show the importance of the variation of alkoxylation backbones.

Method For Octane Requirement Reduction and Octane Requirement Increase Control The purpose of octane requirement tests in engine dynamometer cells is to provide a method of determining the effect of various gasoline components and additives upon the octane requirement of the engine. Measurement of the effect of the induction system and combustion chamber deposits on octane requirement may also be performed.

Engines from vehicles are installed in dynamometer cells in such a way as to simulate road operation using a cycle of idle, low speed and high speed components while carefully controlling specific operating parameters. Two types of octane requirement test are conducted: octane requirement increase control and octane requirement reduction. Contribution of specific deposits to octane requirement may also be determined.

Prior to testing, each engine is inspected and has its induction system cleaned. Parts are checked for excessive wear and a new oil filter, fuel filter, intake valves and spark plugs are installed.

Octane requirement is measured initially with the clean engine, then at specific intervals, until a stable requirement is established. Test stand engines reach an octane stabilization in about 250 hours, or 9500 miles equivalent (168 hours per week). After stabilization, the engine is disassembled, cleaned, reassembled and the octane requirement measured again. This second clean engine octane requirement is referred to as "check back" since it checks back to the initial requirement. The check back octane requirement is the test reference, as it accommodates engine changes that occur throughout the test. A check back octane requirement significantly different from the initial requirement indicates a problem with the test. The difference between the check back octane requirement and the stable octane requirement is the octane requirement increase achieved during the test.

The entire process is repeated using the test gasoline. An octane requirement level established by the test gasoline less than the base gasoline represents octane requirement increase control favorable to the test gasoline.

Octane requirement reduction is a performance feature that demonstrates a reduction from the established octane requirement of a base gasoline in a given engine. The test need not start with a clean engine. The test protocol requires measurement of the octane requirement of an engine fueled with a base gasoline which generally consists of the test gasoline without additives or special treatment. However, the base gasoline may contain additives for a specific comparison. After reaching a stable octane requirement with the base gasoline, the engine is operated on test gasoline until the octane requirement again stabilizes. Rating intervals for test stands are typically twenty-four hours. Test stand engines may be used to conduct several octane requirement reduction tests in sequence with the engine being restabilized on base gasoline between each test. A stable reduction of octane requirement from that of the base gasoline represents octane requirement reduction favorable to the test gasoline.

TABLE 7

OCTANE REQUIREMENT INCREASE CONTROL TESTING
All tests were conducted using 200 ppm by weight of Example 1.

| Test Engine | Fuel | Base Fuel Octane Requirement Minus Test Fuel Octane Requirement* |
|---|---|---|
| 1989 3.8 L Buick | PU | 5 |
| " | RU | 1 |

TABLE 7-continued

OCTANE REQUIREMENT INCREASE
CONTROL TESTING
All tests were conducted using 200 ppm
by weight of Example 1.

| Test Engine | Fuel | Base Fuel Octane Requirement Minus Test Fuel Octane Requirement* |
|---|---|---|
| 1990 3.1 L Chev | PU | 3 |
| " | RU | 1 |
| 1991 3.3 L Dodge | PU | 0 |
| 1987 2.3 L Ford | PU | 3 |
| 1988 2.3 L Olds | PU | 2 |

*Positive numbers indicate good octane control performance.

The overall results indicate that the compound of Example 1 possesses the ability to control octane requirement increase relative to the base fuel in the majority of engines tested.

TABLE 8

OCTANE REQUIREMENT REDUCTION TESTING
All tests were conducted using 200 ppm by weight of
the compound indicated.

| Compound Example # | Test Engine | Fuel | Base Fuel Octane Requirement Minus Test Fuel Octane Requirement* |
|---|---|---|---|
| 1 | 1989 3.8 L Buick | RU | 0 |
| 1 | " | PU | 2 |
| 1 | 1990 3.1 L Chev | PU | 4 |
| 1 | " | PU plus Deposit Control Package** | 3 |
| 1 | " | RU | 2 |
| 1 | 1991 3.3 L Dodge | PU | −3 |
| 1 | 1987 2.3 L Ford | PU | 3 |
| 1 | 1988 2.3 L Olds | PU | 3 |
| 9 | 1990 3.1 L Chev | PU | 3 |

*Positive numbers indicate good octane requirement reduction performance.
**The base fuel contains an additive package comprising a PIB amine and a synthetic carrier for comparative purposes.

The overall results indicate that the compound of Example 1 possesses the ability to reduce octane requirement relative to the base fuel in the majority of the engines tested. Limited engine tests utilizing Example 9 also show a tendency for octane requirement reduction.

Induction System Deposit Test.

The induction system deposit test is a measure of detergency performance in the manifold/valve/port area of an engine induction system. The test involves spraying a mixture of test gasoline and lubricating oil on a hot aluminum tube. The test measures the tendency of the additive package to disperse the carbonaceous deposit generated on the tube. The clean area at the center of the deposit ring on the tube is measured. Generally, the more the deposit is dispersed, the better the manifold/valve/port detergency performance of the gasoline or additive tested. Experience has shown that gasolines giving above about 200 square millimeters clean area provide good intake valve detergency performance, while those giving below about 120 square millimeters are not effective inlet valve detergents. Base fuels give zero clean area. The test conditions are as follows:

| | |
|---|---|
| Spray Nozzle Air Pressure: | 8 psi |
| Air Flow: | 12 l/min |
| Nitrogen Pressure on Test Fuel: | 4.8 psi |
| Test Fuel Volume: | 100 cc |
| Test Fuel Flow: | 2 cc/min |
| Aluminum Tube Temperature: | 260° C. ± 3° C. |
| Oil, Shell Fire & Ice ™ 10W/40: | 0.2 cc/100 cc Fuel |

TABLE 9

| Compound Example # | Concentration ppm by Weight | Clean Area Sq. mm |
|---|---|---|
| — | 0 | 0 |
| 3 | 200 ppm | 38 |
| 1 | 200 ppm | 209 |

A significantly better dispersity is demonstrated utilizing the compound of Example 1 when compared to the compound of Example 3. This demonstrates the importance of structure in determining deposits.

BMW TESTS 10,000 Mile tests to determine intake valve deposits were conducted in 1985 BMW 318i cars having in-line, four cylinder, 4-stroke, water cooled gasoline engines that have a single overhead camshaft, two valves per cylinder and a displacement of 1.8 liters. The engines were port fuel injected equipped with Bosch port fuel-injectors and L-Jetronic fuel management systems. All cars used were equipped with overdrive automatic transmissions.

Before the test started, all combustion chamber deposits were removed from the engine head, intake manifold and piston tops. New intake valves were weighed and installed. The oil and filters were changed, new spark plugs were installed and the fuel injectors flow checked. Mileage was accumulated on public roads using trained drivers. The test route consisted of about 10% city driving (varied speeds with stop-and-go idling), 20% on secondary roads (moderate speeds with infrequent stops) and 70% highway driving (maximum speed of 65 mph).

The primary test data was the intake valve deposits weights at the end of the 10,000 mile test. BMW's pass criteria are as follows: an average deposit weight of 100 milligrams/valve or less at the conclusion of the 10,000 mile test meets BMW requirements for unlimited mileage acceptance; an average deposit weight of 250 mg/valve or less at the conclusion of the test meets BMW's requirement for 50,000 mile service.

| BMW 318i Test Results | | | | | |
|---|---|---|---|---|---|
| Compound Example # | Concentration ppm by wt. | Additional Detergent | Concentration ppm by wt. | Fuel | Average Deposit Wt. at miles × 1000 |
| 1 | 200 | — | — | PU | 37 mg at 10 |
| 1 | 200 | — | — | RU | 111 mg at 5 |
| 1 | 300 | — | — | RU | 254 mg at 5 |
| 1 | 200 | PPO[1] | 125 | RU | 152 mg at 5 |
| 1 | 200 | PIB[2] | 300 | RU | 128 mg at 5 |
| 1 | 160 | PIB-DAP[3] | 90 | RU | 42 mg at 5 |
| 1 | 160 | PIB-DAP[3] | 90 | RU | 65 mg at 10 |
| 1 | 200 | PPO[1] | 250 | RU | 87 mg at 5 |

-continued

| | | BMW 318i Test Results | | | |
|---|---|---|---|---|---|
| Compound Example # | Concentration ppm by wt. | Additional Detergent | Concentration ppm by wt. | Fuel | Average Deposit Wt. at miles × 1000 |
| 1 | 125 | PIB-DAP[3] | 125 | RU | 1.4 mg at 5 |
| 1 | 125 | PIB-DAP[3] | 125 | RU | 51 mg at 10 |
| 1 | 125 | PBO[4] | 200 | RU | 100 mg at 5 |
| 1 | 200 | PIB-DAP[3] | 50 | RU | 326 mg at 5 |
| 1 | 150 | OGA-480[5] | 100 | RU | 131 mg at 5 |
| 1 | 200 | PIB-DAP[3] | 75 | RU | 91 mg at 10 |

[1]PPO = polypropylene oxide, Mw = 1600.
[2]PIB = polyisobutylene, Mw = 750.
[3]PIB-DAP = N-polyisobutyenyl-N',N'-dimethyl-1,3-diaminopropane, Mw = 1050.
[4]PBO = poly(butylene)oxide, Mw = 1450.
[5]OGA-480 = a poly(oxyalkylene)carbamate available commerically from Oronite.
The results of Table 10 demonstrate the advantages of using the compounds of the present invention alone and in formulations with other existing detergents and carrier fluids.

What is claimed is:

1. A fuel composition comprising a mixture of a major amount of hydrocarbons in the gasoline boiling range and a minor amount of an additive compound having the general formula:

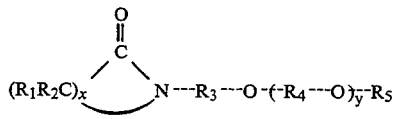

wherein x is from 3 to 11; y is from 1 to 50; $R_1$ and $R_2$ are independently selected from the group consisting of hydrogen, hydrocarbyl of 1 to 100 carbon atoms and substituted hydrocarbyl of 1 to 100 carbon atoms; $R_3$ is selected from the group consisting of hydrocarbyl of 1 to 100 carbon atoms and substituted hydrocarbyl of 1 to 100 carbon atoms; $R_4$ is independently selected from the group consisting of hydrocarbyl of 2 to 100 carbon atoms and substituted hydrocarbyl of 2 to 100 carbon atoms; $R_5$ is selected from the group consisting of hydrogen, hydrocarbyl of 1 to 100 carbon atoms, substituted hydrocarbyl of 1 to 100 carbon atoms and acyl of 1 to 20 carbon atoms and the weight average molecular weight of the additive compound is at least about 600.

2. The fuel composition of claim 1 wherein $R_4$ has the formula:

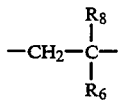

wherein $R_8$ is independently selected from the group consisting of hydrogen, hydrocarbyl of 1 to 18 carbon atoms and substituted hydrocarbyl of 1 to 18 carbon atoms and $R_6$ is independently selected from the group consisting of hydrogen, hydrocarbyl of 1 to 18 carbon atoms and substituted hydrocarbyl of 1 to 18 carbon atoms.

3. The fuel composition of claim 2 wherein said additive compound is present in an amount from about 50 ppm by weight to about 400 ppm by weight based on the total weight of the fuel composition.

4. The fuel composition of claim 3 wherein the weight average molecular weight of the additive compound is from about 800 to about 4000.

5. The fuel composition of claim 4 wherein y is from 8 to 40.

6. The fuel composition of claim 5 wherein $R_3$ is hydrocarbyl of 1 to 20 carbon atoms or substituted hydrocarbyl of 1 to 20 carbon atoms.

7. The fuel composition of claim 6 wherein $R_1$ and $R_2$ are each hydrogen.

8. The fuel composition of claim 7 wherein x is 3; $R_3$ is hydrocarbyl of two carbon atoms; $R_6$ is independently hydrogen or hydrocarbyl comprising alkyl of 1 to 2 carbon atoms; $R_8$ is hydrogen; and $R_5$ is hydrogen.

9. The fuel composition of claim 7 wherein x is 3; $R_3$ is hydrocarbyl of four carbon atoms; $R_6$ is independently hydrogen or hydrocarbyl comprising alkyl of 1 to 2 carbon atoms; $R_8$ is hydrogen; and $R_5$ is hydrogen.

10. The fuel composition of claim 5 wherein $R_1$ and $R_2$ are independently hydrogen or hydrocarbyl of 1 to 8 carbon atoms; $R_3$ is hydrocarbyl of 2 or 4 carbon atoms; $R_5$ is hydrogen; $R_6$ is independently hydrogen, hydrocarbyl comprising alkyl of 1 to 18 carbon atoms or substituted hydrocarbyl comprising oxy-substituted hydrocarbyl of 1 to 18 carbon atoms; and $R_8$ is hydrogen.

11. The fuel composition of claim 10 wherein in $R_6$ the oxy-substituted hydrocarbyl is selected from the group consisting of ethylhexyleneoxymethylene, isopropoxymethylene, butoxymethylene and mixtures thereof.

12. The fuel composition of claim 10 wherein in $R_6$ the oxy-substituted hydrocarbyl is selected from the group consisting of nonylphenoxymethylene, phenoxymethylene and mixtures thereof.

13. The fuel composition of claim 6 wherein x is 5; $R_3$ is hydrocarbyl of four carbon atoms; $R_6$ is independently hydrogen or hydrocarbyl comprising alkyl of 1 to 2 carbon atoms; $R_8$ is hydrogen; and $R_5$ is hydrogen.

14. The fuel composition of claim 13 wherein $R_1$ and $R_2$ are independently hydrogen or hydrocarbyl comprising alkyl of 1 to 8 carbon atoms.

15. The fuel composition of claim 6 wherein x is 5; $R_1$ and $R_2$ are hydrogen; $R_3$ is hydrocarbyl of four carbon atoms; $R_6$ is independently hydrogen, hydrocarbyl comprising alkyl of 1 to 2 carbon atoms, substituted hydrocarbyl comprising alkoxy-substituted alkylene of 1 to 18 carbon atoms or substituted hydrocarbyl comprising aryloxy-substituted alkylene of 1 to 18 carbon atoms; $R_8$ is hydrogen; and $R_5$ is hydrogen.

16. The fuel composition of claim 1 wherein $R_4$ has the formula:

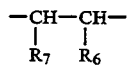

wherein $R_7$ is independently selected from the group consisting of hydrogen, hydrocarbyl of 1 to 18 carbon atoms and substituted hydrocarbyl of 1 to 18 carbon atoms; $R_6$ is independently selected from the group consisting of hydrogen, hydrocarbyl of 1 to 18 carbon atoms and substituted hydrocarbyl of 1 and 18 carbon atoms; $R_1$ and $R_2$ are hydrogen; $R_3$ is hydrocarbyl of two carbon atoms; and $R_5$ is hydrogen.

17. A fuel composition comprising a mixture of a major amount of hydrocarbons in the gasoline boiling range and an additive compound in an amount from about 50 ppm by weight to about 400 ppm by weight based on the total weight of the fuel composition having the general formula:

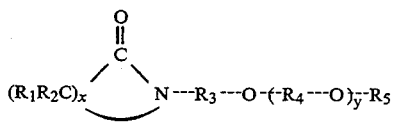

wherein x is 3; y is from 18 to 24; $R_1$ and $R_2$ are hydrogen; $R_3$ is alkylene of 2 carbon atoms; $R_4$ is hydrocarbyl of the formula:

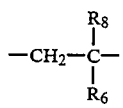

wherein $R_8$ is hydrogen and $R_6$ is alkyl of 2 carbon atoms; $R_5$ is hydrogen and the weight average molecular weight of the additive compound is from about 1000 to about 2000.

18. A fuel composition comprising a mixture of a major amount of hydrocarbons in the gasoline boiling range and an additive compound in an amount from about 50 ppm by weight to about 400 ppm by weight based on the total weight of the fuel composition having the general formula:

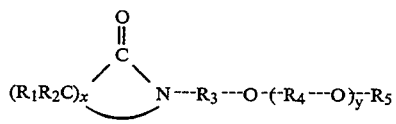

wherein x is 5; y is from 18 to 24; $R_1$ and $R_2$ are hydrogen; $R_3$ is alkylene of 4 carbon atoms; $R_4$ is hydrocarbyl of the formula:

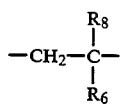

wherein $R_8$ is hydrogen and $R_6$ is alkyl of 2 carbon atoms; $R_5$ is hydrogen and the weight average molecular weight of the additive compound is from about 1000 to about 2000.

19. A fuel composition comprising a mixture of a major amount of hydrocarbons in the gasoline boiling range and an additive compound in an amount from about 50 ppm by weight to about 400 ppm by weight based on the total weight of the fuel composition having the general formula:

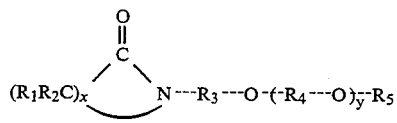

wherein x is 3; y is from 8 to 40; $R_1$ and $R_2$ are hydrogen; $R_3$ is alkylene of 2 carbon atoms; $R_4$ independently has the formula:

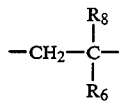

wherein $R_8$ and $R_6$ are independently selected from the group consisting of hydrogen, alkyl of 1 to 18 carbon atoms, alkoxy-substituted alkylene of 1 to 18 carbon atoms and aryloxy-substituted alkylene of 1 to 18 carbon atoms; $R_5$ is hydrogen and the weight average molecular weight of the additive compound is from about 1000 to about 2000.

20. A method for controlling the octane requirement increase in an internal combustion engine which comprises burning in said engine a fuel composition comprising a major amount of hydrocarbons in the gasoline boiling range and a minor amount of an additive compound having the formula:

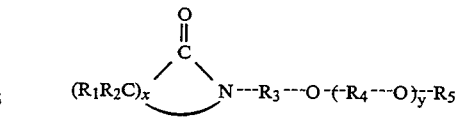

wherein x is from 3 to 11; y is from 1 to 50; $R_1$ and $R_2$ are independently selected from the group consisting of hydrogen, hydrocarbyl of 1 to 100 carbon atoms and substituted hydrocarbyl of 1 to 100 carbon atoms; $R_3$ is selected from the group consisting of hydrocarbyl of 1 to 100 carbon atoms and substituted hydrocarbyl of 1 to 100 carbon atoms; $R_4$ is independently selected from the group consisting of hydrocarbyl of 2 to 100 carbon atoms and substituted hydrocarbyl of 2 to 100 carbon atoms; $R_5$ is selected from the group consisting of hydrogen, hydrocarbyl of 1 to 100 carbon atoms, substituted hydrocarbyl of 1 to 100 carbon atoms and acyl of 1 to 20 carbon atoms; ant eh weight average molecular weight of the additive compound is at least about 600.

21. The method of claim 20 wherein $R_4$ has the formula:

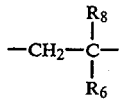

wherein $R_8$ is independently selected from the group consisting of hydrogen, hydrocarbyl of 1 to 18 carbon atoms and substituted hydrocarbyl of 1 to 18 carbon atoms and $R_6$ is independently selected from the group consisting of hydrogen, hydrocarbyl of 1 to 18 carbon atoms and substituted hydrocarbyl of 1 to 18 carbon atoms.

22. The method of claim 21 wherein said additive compound is present in an amount from about 50 ppm by weight to about 400 ppm by weight based on the total weight of the fuel composition.

23. The method of claim 22 wherein the weight average molecular weight of the additive compound is from about 800 to about 4000.

24. The method of claim 23 wherein y is from 8 to 40.

25. The method of claim 24 wherein $R_3$ is hydrocarbyl of 1 to 20 carbon atoms or substituted hydrocarbyl of 1 to 20 carbon atoms.

26. The method of claim 25 wherein $R_1$ and $R_2$ are each hydrogen

27. The method of claim 26 wherein x is 3; $R_3$ is hydrocarbyl of two carbon atoms; $R_6$ is independently hydrogen or hydrocarbyl comprising alkyl of 1 to 2 carbon atoms; $R_8$ is hydrogen; and $R_5$ is hydrogen.

28. The method of claim 26 wherein x is 3; $R_3$ is hydrocarbyl of four carbon atoms; $R_6$ is independently hydrogen or hydrocarbyl comprising alkyl of 1 to 2 carbon atoms; $R_8$ is hydrogen; and $R_5$ is hydrogen.

29. The method of claim 24 wherein $R_1$ and $R_2$ are independently hydrogen or hydrocarbyl of 1 to 8 carbon atoms; $R_3$ is hydrocarbyl of 2 or 4 carbon atoms; $R_5$ is hydrogen; $R_6$ is independently hydrogen, hydrocarbyl comprising alkyl of 1 to 18 carbon atoms or substituted hydrocarbyl comprising oxy-substituted hydrocarbyl of 1 to 18 carbon atoms; and $R_8$ is hydrogen.

30. The method of claim 29 wherein in $R_6$ the oxy-substituted hydrocarbyl selected from the group consisting of ethylhexyleneoxymethylene, isopropoxymethylene, butoxymethylene and mixtures thereof.

31. The method of claim 29 wherein in $R_6$ the oxy-substituted hydrocarbyl is selected from the group consisting of nonylphenoxymethylene, phenoxymethylene and mixtures thereof.

32. The method of claim 25 wherein x is 5; $R_3$ is hydrocarbyl of four carbon atoms; $R_6$ is independently hydrogen or hydrocarbyl comprising alkyl of 1 to 2 carbon atoms; $R_8$ is hydrogen; and $R_5$ is hydrogen.

33. The method of claim 32 wherein $R_1$ and $R_2$ are independently hydrogen or alkyl of 1 to 8 carbon atoms.

34. The method of claim 25 wherein x is 5; $R_1$ and $R_2$ are hydrogen; $R_3$ is hydrocarbyl of four carbon atoms; $R_6$ is independently hydrogen, hydrocarbyl comprising alkyl of 1 to 2 carbon atoms, substituted hydrocarbyl comprising alkoxy-substituted alkylene of 1 to 18 carbon atoms or substituted hydrocarbyl comprising aryloxy substituted alkylene of 1 to 18 carbon atoms; $R_8$ is hydrogen; and $R_5$ is hydrogen.

35. The method of claim 20 wherein $R_4$ has the formula:

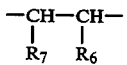

wherein $R_7$ is independently selected from the group consisting of hydrogen, hydrocarbyl of 1 to 18 carbon atoms and substituted hydrocarbyl of 1 to 18 carbon atoms; $R_6$ is independently selected from the group consisting of hydrogen, hydrocarbyl of 1 to 18 carbon atoms and substituted hydrocarbyl of 1 to 18 carbon atoms; $R_1$ and $R_2$ are hydrogen; $R_3$ is hydrocarbyl of two carbon atoms; and $R_5$ is hydrogen.

36. A method for reducing octane requirement in an internal combustion engine which comprises burning in said engine a fuel composition comprising a major amount of hydrocarbons in the gasoline boiling range and a minor amount of an additive compound having the formula:

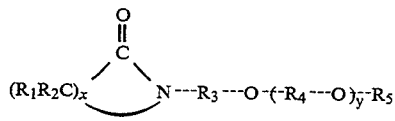

wherein x is from 3 to 11; y is from 1 to 50; $R_1$ and $R_2$ are independently selected from the group consisting of hydrogen, hydrocarbyl of 1 to 100 carbon atoms and substituted hydrocarbyl of 1 to 100 carbon atoms; $R_3$ is selected from the group consisting of hydrocarbyl of 1 to 100 carbon atoms and substituted hydrocarbyl of 1 to 100 carbon atoms; $R_4$ is independently selected from the group consisting of hydrocarbyl of 2 to 100 carbon atoms and substituted hydrocarbyl of 2 to 100 carbon atoms; $R_5$ is selected from the group consisting of hydrogen, hydrocarbyl of 1 to 100 carbon atoms, substituted hydrocarbyl of 1 to 100 carbon atoms and acyl of 1 to 20 carbon atoms and the weight average molecular weight of the additive compound is at least about 600.

37. The method of claim 36 wherein $R_4$ has the formula:

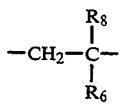

wherein $R_8$ is independently selected from the group consisting of hydrogen, hydrocarbyl of 1 to 18 carbon atoms and substituted hydrocarbyl of 1 to 18 carbon atoms and $R_6$ is independently selected from the group consisting of hydrogen, hydrocarbyl of 1 to 18 carbon atoms and substituted hydrocarbyl of 1 to 18 carbon atoms.

38. The method of claim 37 wherein said additive compound is present in an amount from about 50 ppm by weight to about 400 ppm by weight based on the total weight of the fuel composition.

39. The method of claim 38 wherein the weight average molecular weight of the additive compound is from about 800 to about 4000.

40. The method of claim 39 wherein y is from 8 to 40.

41. The method of claim 40 wherein $R_3$ is hydrocarbyl of 1 to 20 carbon atoms or substituted hydrocarbyl of 1 to 20 carbon atoms.

42. The method of claim 41 wherein $R_1$ and $R_2$ are each hydrogen.

43. The method of claim 42 wherein x is 3; $R_3$ is hydrocarbyl of two carbon atoms; $R_6$ is independently hydrogen or hydrocarbyl comprising alkyl of 1 to 2 carbon atoms; $R_8$ is hydrogen; and $R_5$ is hydrogen.

44. The method of claim 42 wherein x is 3; $R_3$ is hydrocarbyl of four carbon atoms; $R_6$ is independently hydrogen or hydrocarbyl comprising alkyl of 1 to 2 carbon atoms; $R_8$ is hydrogen; and $R_5$ is hydrogen.

45. The method of claim 40 wherein $R_1$ and $R_2$ are independently hydrogen or hydrocarbyl of 1 to 8 carbon atoms; $R_3$ is hydrocarbyl of 2 or 4 carbon atoms; $R_5$ is hydrogen; $R_6$ is independently hydrogen, hydrocarbyl comprising alkyl of 1 to 18 carbon atoms or substituted hydrocarbyl comprising oxy-substituted hydrocarbyl of 1 to 18 carbon atoms; and $R_8$ is hydrogen.

46. The method of claim 45 wherein in $R_6$ the oxy-substituted hydrocarbyl selected from the group consisting of ethylhexyleneoxymethylene, isopropoxymethylene, butoxymethylene and mixtures thereof.

47. The method of claim 45 wherein in $R_6$ the oxy-substituted hydrocarbyl is selected from the group consisting of nonylphenoxymethylene, phenoxymethylene and mixtures thereof.

48. The method of claim 41 wherein x is 5; $R_3$ is hydrocarbyl of four carbon atoms; $R_6$ is independently hydrogen or hydrocarbyl comprising alkyl of 1 to 2 carbon atoms; $R_8$ is hydrogen; and $R_5$ is hydrogen.

49. The method of claim 48 wherein $R_1$ and $R_2$ are independently hydrogen or hydrocarbyl comprising alkyl of 1 to 8 carbon atoms.

50. The method of claim 41 wherein x is 5; $R_1$ and $R_2$ are hydrogen; $R_3$ is hydrocarbyl of four carbon atoms; $R_6$ is independently hydrogen, hydrocarbyl comprising alkyl of 1 to 2 carbon atoms, substituted hydrocarbyl comprising alkoxy-substituted alkylene of 1 to 18 carbon atoms or substituted hydrocarbyl comprising aryloxy-substituted alkylene of 1 to 18 carbon atoms; $R_8$ is hydrogen; and $R_5$ is hydrogen.

51. The method of claim 36 wherein $R_4$ has the formula:

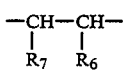

wherein $R_7$ is independently selected from the group consisting of hydrogen, hydrocarbyl of 1 to 18 carbon atoms and substituted hydrocarbyl of 1 to 18 carbon atoms; $R_6$ is independently selected from the group consisting of hydrogen, hydrocarbyl of 1 to 18 carbon atoms and substituted hydrocarbyl of 1 to 18 carbon atoms; $R_1$ and $R_2$ are hydrogen; $R_3$ is hydrocarbyl of two carbon atoms; and $R_5$ is hydrogen.

52. A method for reducing intake valve deposits in an internal combustion engine which comprises burning in said engine a fuel composition comprising a major amount of hydrocarbons in the gasoline boiling range and a minor amount of an additive compound having the formula:

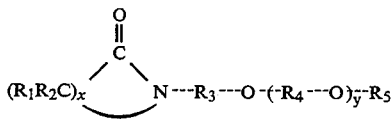

wherein x is from 3 to 11; y is from 1 to 50; $R_1$ and $R_2$ are independently selected from the group consisting of hydrogen, hydrocarbyl of 1 to 100 carbon atoms and substituted hydrocarbyl of 1 to 100 carbon atoms; $R_3$ is selected from the group consisting of hydrocarbyl of 1 to 100 carbon atoms and substituted hydrocarbyl of 1 to 100 carbon atoms; $R_4$ is independently selected from the group consisting of hydrocarbyl of 2 to 100 carbon atoms and substituted hydrocarbyl of 2 to 100 carbon atoms; $R_5$ is selected from the group consisting of hydrogen, hydrocarbyl of 1 to 100 carbon atoms, substituted hydrocarbyl of 1 to 100 carbon atoms and acyl of 1 to 20 carbon atoms and the weight average molecular weight of the additive compound is at least about 600.

53. The method of claim 52 wherein $R_4$ has the formula:

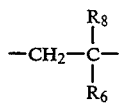

wherein $R_8$ is independently selected from the group consisting of hydrogen, hydrocarbyl of 1 to 18 carbon atoms and substituted hydrocarbyl of 1 to 18 carbon atoms and $R_6$ is independently selected from the group consisting of hydrogen, hydrocarbyl of 1 to 18 carbon atoms and substituted hydrocarbyl of 1 to 18 carbon atoms.

54. The method of claim 53 wherein said additive compound is present in an amount from about 50 ppm by weight to about 400 ppm by weight based on the total weight of the fuel composition.

55. The method of claim 54 wherein the weight average molecular weight of the additive compound is from about 800 to about 4000.

56. The method of claim 55 wherein y is from 8 to 40.

57. The method of claim 56 wherein $R_3$ is hydrocarbyl of 1 to 20 carbon atoms or substituted hydrocarbyl of 1 to 20 carbon atoms.

58. The method of claim 57 wherein $R_1$ and $R_2$ are each hydrogen.

59. The method of claim 68 wherein x is 3; $R_3$ is hydrocarbyl of two carbon atoms; $R_6$ is independently hydrogen or hydrocarbyl comprising alkyl of 1 to 2 carbon atoms; $R_8$ is hydrogen; and $R_5$ is hydrogen.

60. The method of claim 58 wherein x is 3; $R_3$ is hydrocarbyl of four carbon atoms; $R_6$ is independently hydrogen or hydrocarbyl comprising from alkyl of 1 to 2 carbon atoms; $R_8$ is hydrogen; and $R_5$ is hydrogen.

61. The method of claim 56 wherein $R_1$ and $R_2$ are independently hydrogen or hydrocarbyl of 1 to 8 carbon atoms; $R_3$ is hydrocarbyl of 2 or 4 carbon atoms; $R_5$ is hydrogen; $R_6$ is independently hydrogen, hydrocarbyl comprising alkyl of 1 to 18 carbon atoms or substituted hydrocarbyl comprising oxy-substituted hydrocarbyl of 1 to 18 carbon atoms; and $R_8$ is hydrogen.

62. The method of claim 61 wherein in $R_6$ the oxy-substituted hydrocarbyl selected from the group consisting of ethylhexyleneoxymethylene, isopropoxymethylene, butoxymethylene and mixtures thereof.

63. The method of claim 61 wherein in $R_6$ the oxy-substituted hydrocarbyl is selected from the group consisting of nonylphenoxymethylene, phenoxymethylene and mixtures thereof.

64. The method of claim 57 wherein x is 5; $R_3$ is hydrocarbyl of four carbon atoms; $R_6$ is independently hydrogen or hydrocarbyl comprising alkyl of 1 to 2 carbon atoms; $R_8$ is hydrogen; and $R_5$ is hydrogen.

65. The method of claim 64 wherein $R_1$ and $R_2$ are independently hydrogen or hydrocarbyl comprising alkyl of 1 to 8 carbon atoms.

66. The method of claim 57 wherein x is 5; $R_1$ and $R_2$ are hydrogen; $R_3$ is hydrocarbyl of four carbon atoms; $R_6$ is independently hydrogen, hydrocarbyl comprising alkyl of 1 to 2 carbon atoms, substituted hydrocarbyl comprising alkoxy-substituted alkylene of 1 to 18 carbon atoms or substituted hydrocarbyl comprising aryloxy-substituted alkylene of 1 to 18 carbon atoms; $R_8$ is hydrogen; and $R_5$ is hydrogen.

67. The method of claim 52 wherein $R_4$ has the formula:

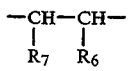

wherein $R_7$ is independently selected from the group consisting of hydrogen, hydrocarbyl of 1 to 18 carbon atoms and substituted hydrocarbyl of 1 to 18 carbon atoms; $R_6$ is independently selected from the group consisting of hydrogen, hydrocarbyl of 1 to 18 carbon atoms and substituted hydrocarbyl of 1 to 18 carbon atoms; $R_1$ and $R_2$ are hydrogen; $R_3$ is hydrocarbyl of two carbon atoms; and $R_5$ is hydrogen.

68. A compound having the formula:

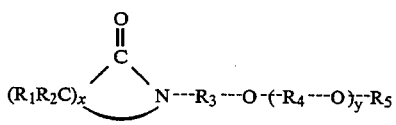

wherein x is 3; y is from 18 to 24; $R_1$ and $R_2$ are hydrogen; $R_3$ is alkylene of 2 carbon atoms; $R_4$ is hydrocarbyl of the formula:

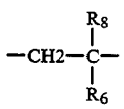

wherein $R_8$ is hydrogen and $R_6$ is alkyl of 2 carbon atoms; and $R_5$ is hydrogen.

69. A fuel composition comprising a mixture of:
   (a) a major amount of hydrocarbons in the gasoline boiling range;
   (b) a minor amount of an additive compound having the general formula:

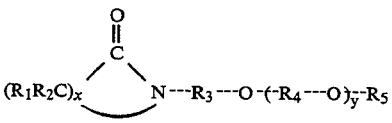

wherein x is from 3 to 11; y is from 1 to 50; $R_1$ and $R_2$ are independently selected from the group consisting of hydrogen, hydrocarbyl of 1 to 100 carbon atoms and substituted hydrocarbyl of 1 to 100 carbon atoms; $R_3$ is selected from the group consisting of hydrocarbyl of 1 to 100 carbon atoms and substituted hydrocarbyl of 1 to 100 carbon atoms; $R_4$ is independently selected from the group consisting of hydrocarbyl of 2 to 100 carbon atoms and substituted hydrocarbyl of 2 to 100 carbon atoms; $R_5$ is selected from the group consisting of hydrogen, hydrocarbyl of 1 to 100 carbon atoms, substituted hydrocarbyl of 1 to 100 carbon atoms and acyl of 1 to 20 carbon atoms and the weight average molecular weight of the compound is at least about 600; and
   (c) a minor amount of an additional detergent selected from the group consisting of polyalkenyl amines, mannich amines, polyalkenyl succinimides, poly(oxyalkylene) carbamates, poly(alkenyl)-N-substituted carbamates and mixture thereof.

70. The fuel composition of claim 69 wherein $R_4$ has the formula:

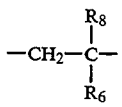

wherein $R_8$ is independently selected from the group consisting of hydrogen, hydrocarbyl of 1 to 18 carbon atoms and substituted hydrocarbyl of 1 to 18 carbon atoms and $R_6$ is independently selected from the group consisting of hydrogen, hydrocarbyl of 1 to 18 carbon atoms and substituted hydrocarbyl of 1 to 18 carbon atoms.

71. The fuel composition of claim 70 wherein the additive compound is present in an amount from about 50 ppm by weight to about 400 ppm by weight based on the total weight of the fuel composition.

72. The fuel composition of claim 71 wherein the weight average molecular weight of the additive compound is from about 800 to about 4000.

73. The fuel composition of claim 72 wherein y is from 8 to 40; $R_3$ is selected from the group consisting of hydrocarbyl of 1 to 20 carbon atoms and substituted hydrocarbyl of 1 to 20 carbon atoms.

74. The fuel composition of claim 73 wherein $R_1$ and $R_2$ are each hydrogen; x is 3; $R_3$ is hydrocarbyl of two carbon atoms; $R_6$ is independently hydrogen or hydrocarbyl comprising alkyl of 1 to 2 carbon atoms; $R_8$ is hydrogen; and $R_5$ is hydrogen.

75. The fuel composition of claim 73 wherein $R_1$ and $R_2$ are each hydrogen; x is 3; $R_3$ is hydrocarbyl of four carbon atoms; $R_6$ is independently hydrogen or hydrocarbyl comprising alkyl of 1 to 2 carbon atoms; $R_8$ is hydrogen; and $R_5$ is hydrogen.

76. The fuel composition of claim 73 wherein $R_1$ and $R_2$ are each hydrogen; x is 5; $R_3$ is hydrocarbyl of four carbon atoms; $R_6$ is independently hydrogen or hydrocarbyl comprising alkyl of 1 to 2 carbon atoms; $R_8$ is hydrogen; and $R_5$ is hydrogen.

77. The fuel composition of claim 69 wherein $R_4$ has the formula:

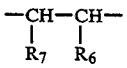

wherein $R_7$ is independently selected from the group consisting of hydrogen, hydrocarbyl of 1 to 18 carbon atoms and substituted hydrocarbyl of 1 to 18 carbon atoms; $R_6$ is independently selected from the group consisting of hydrogen, hydrocarbyl of 1 to 18 carbon atoms and substituted hydrocarbyl of 1 to 18 carbon atoms.

78. The fuel composition of claim 77 wherein the additive compound is present in an amount from about 50 ppm by weight to about 400 ppm by weight based on the total weight of the fuel composition.

79. The fuel composition of claim 78 wherein the weight average molecular weight of the additive compound is from about 800 to about 4000.

80. The fuel composition of claim 79 wherein y is from 8 to 40; $R_3$ is selected from the group consisting of hydrocarbyl of 1 to 20 carbon atoms and substituted hydrocarbyl of 1 to 20 carbon atoms.

81. The fuel composition of claim 80 wherein $R_1$ and $R_2$ are each hydrogen; x is 3; $R_3$ is hydrocarbyl of two carbon atoms; $R_6$ is independently hydrogen or hydrocarbyl comprising alkyl of 1 to 2 carbon atoms; $R_8$ is hydrogen; and $R_5$ is hydrogen.

82. The fuel composition of claim 80 wherein $R_1$ and $R_2$ are each hydrogen; x is 3; $R_3$ is hydrocarbyl of four carbon atoms; $R_6$ is independently hydrogen or hydrocarbyl comprising alkyl of 1 to 2 carbon atoms; $R_8$ is hydrogen; and $R_5$ is hydrogen.

83. The fuel composition of claim 80 wherein $R_1$ and $R_2$ are each hydrogen; x is 5; $R_3$ is hydrocarbyl of four carbon atoms; $R_6$ is independently hydrogen or hydrocarbyl comprising alkyl of 1 to 2 carbon atoms; $R_8$ is hydrogen; and $R_5$ is hydrogen.

* * * * *